(12) United States Patent
Banta et al.

(10) Patent No.: US 9,127,267 B2
(45) Date of Patent: Sep. 8, 2015

(54) LEUCINE BETA ROLL DOMAINS AND USES THEREOF

(71) Applicant: THE TRUSTEES OF COLUMBIA UNIVERSITY IN THE CITY OF NEW YORK, New York, NY (US)

(72) Inventors: Scott Banta, Fairfield, CT (US); Mark A. Blenner, Clemson, SC (US); Ian Wheeldon, Riverside, CA (US); Kevin Dooley, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/674,283

(22) Filed: Nov. 12, 2012

(65) Prior Publication Data

US 2013/0237612 A1   Sep. 12, 2013

Related U.S. Application Data

(60) Provisional application No. 61/558,826, filed on Nov. 11, 2011.

(51) Int. Cl.
| | | |
|---|---|---|
| *A01N 25/00* | (2006.01) | |
| *A61K 47/00* | (2006.01) | |
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *A61K 38/04* | (2006.01) | |
| *C12N 9/88* | (2006.01) | |
| *A61L 27/22* | (2006.01) | |
| *A61L 27/50* | (2006.01) | |
| *A61L 27/52* | (2006.01) | |
| *A61L 27/54* | (2006.01) | |
| *A61L 15/32* | (2006.01) | |
| *A61L 15/42* | (2006.01) | |
| *A61L 15/44* | (2006.01) | |
| *A61L 15/46* | (2006.01) | |
| *A61L 15/60* | (2006.01) | |

(52) U.S. Cl.
CPC . *C12N 9/88* (2013.01); *A61L 15/32* (2013.01); *A61L 15/42* (2013.01); *A61L 15/44* (2013.01); *A61L 15/46* (2013.01); *A61L 15/60* (2013.01); *A61L 27/227* (2013.01); *A61L 27/50* (2013.01); *A61L 27/52* (2013.01); *A61L 27/54* (2013.01); *C12Y 406/01001* (2013.01); *A61L 2400/06* (2013.01)

(58) Field of Classification Search
CPC .......... C12N 9/88; A61L 15/32; A61L 27/52; A61L 27/227; A61L 27/50; A61L 15/44; A61L 15/46; A61L 15/60; A61L 27/54; A61L 15/42; A61L 2400/06; C12Y 406/01001
See application file for complete search history.

(56) References Cited

U.S. PATENT DOCUMENTS 7,179,487 B1    2/2007  Kopecek et al.
7,625,951 B2   12/2009  Daunert et al.

FOREIGN PATENT DOCUMENTS

WO   WO-2008/011204         1/2008
WO   WO 2010123945 A2 * 10/2010

OTHER PUBLICATIONS

Blenner et al "Calcium-Induced Folding of a Beta Roll Motif Requires C-Terminal Entropic Stabilization" J Mol Biol 400:244-256. Published online May 11, 2010.*
Petka et al "Reversible Hydrogels from Self-Assembling Artificial Proteins" Science 281:389-392. Published Jul. 17, 1998.*
Wang, Jing Jing, et al., "Photoinduced graft polymerization of 2-methacryloyloxyethyl phosphorylcholine on silicone hydrogels for reducing protein adsorption", J. Mater Sci: Mater Med, 2011, vol. 22, pp. 2651-2657.
Baumann, Ulrich, "Crystal Structure of the 50 kDa Metallo Protease from *Serratia marcescens*", J. Mol. Biol., Sep. 23, 1994, vol. 242, No. 3, pp. 244-251.
Blenner, Mark A., et al., "Calcium-Induced Folding of a Beta Roll Motif Requires C-Terminal Entropic Stabilization", J. Mol. Biol., Jul. 2010, vol. 400, No. 2, pp. 244-256.
Chockalingam, Karuppiah, et al., "Design and application of stimulus-responsive peptide systems", Protein Engineering, Design & Selection, Apr. 2007, vol. 20, No. 4, pp. 155-161.
Crocker, John C., et al., "Two-Point Microrheology of Inhomogenous Soft Materials", Physical Review Letters, Jul. 24, 2000, vol. 85, No. 4, pp. 888-891.
Dooley, Kevin, et al., "Engineering of an Environmentally Responsive Beta Roll Peptide for Use as a Calcium-Dependent Cross-Linking Domain for Peptide Hydrogel Formation", Biomacromolecules, 2012, vol. 13, pp. 1758-1764.
Ehrick, Jason D., et al., "Genetically engineered protein in hydrogels tailors stimuli-responsive characters", Nature Materials, Apr. 2005, vol. 4, pp. 298-302.
LV, Shanshan, et al., "Tandem Modular Protein-Based Hydrogels Constructed Using a Novel Two-Component Approach", Langmuir, 2012, vol. 28, pp. 2269-2274.
Ringler, Philippe, et al., "Self-Assembly of Proteins into Designed Networks", Science, Oct. 3, 2003, vol. 302, pp. 106-109.
Szilvay, Geza R., et al., "A FRET-Based Method for Probing the Conformational Behavior of an Intrinsically Disordered Repeat Domain from *Bordetella pertussis* Adenylate Cyclase", Biochemistry, 2009, vol. 48, pp. 11273-11282.

* cited by examiner

*Primary Examiner* — James H Alstrum Acevedo
*Assistant Examiner* — Zachary J Miknis
(74) *Attorney, Agent, or Firm* — Wiggin and Dana LLP; Anthony P. Gangemi

(57) ABSTRACT

In one aspect, the invention relates to a peptide that forms a calcium-dependent hydrogel using a rationally engineered beta roll peptide. In the absence of calcium, the peptide is intrinsically disordered. Upon addition of calcium, the peptide forms a corkscrew-like structure. In one embodiment, one face of the beta roll is mutated to comprise leucine residues. In some embodiments, a leucine zipper forming helical domain to the engineered beta roll forms hydrogels by physical cross-linking in calcium rich environments.

11 Claims, 13 Drawing Sheets

(2 of 13 Drawing Sheet(s) Filed in Color)

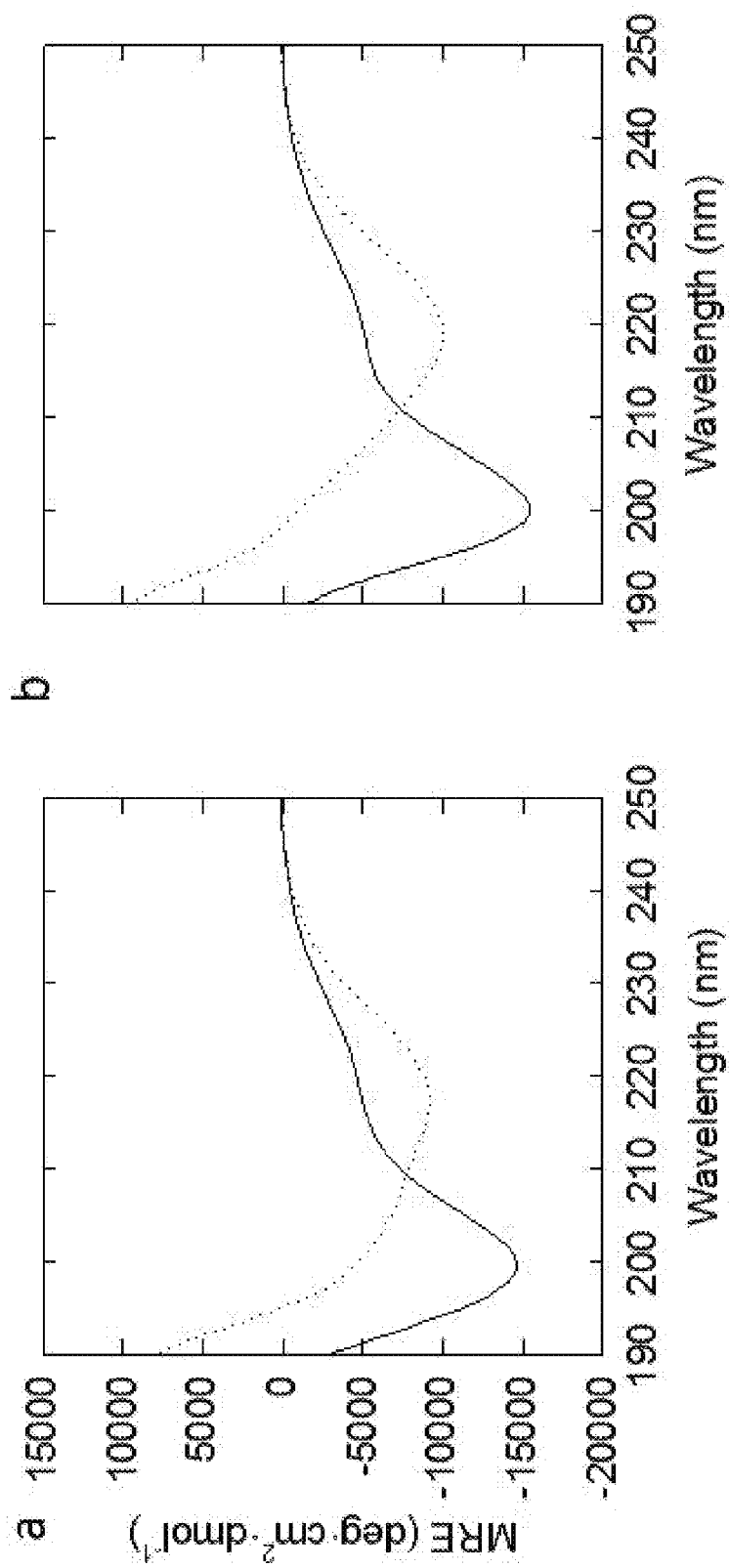
Figure 4a-b

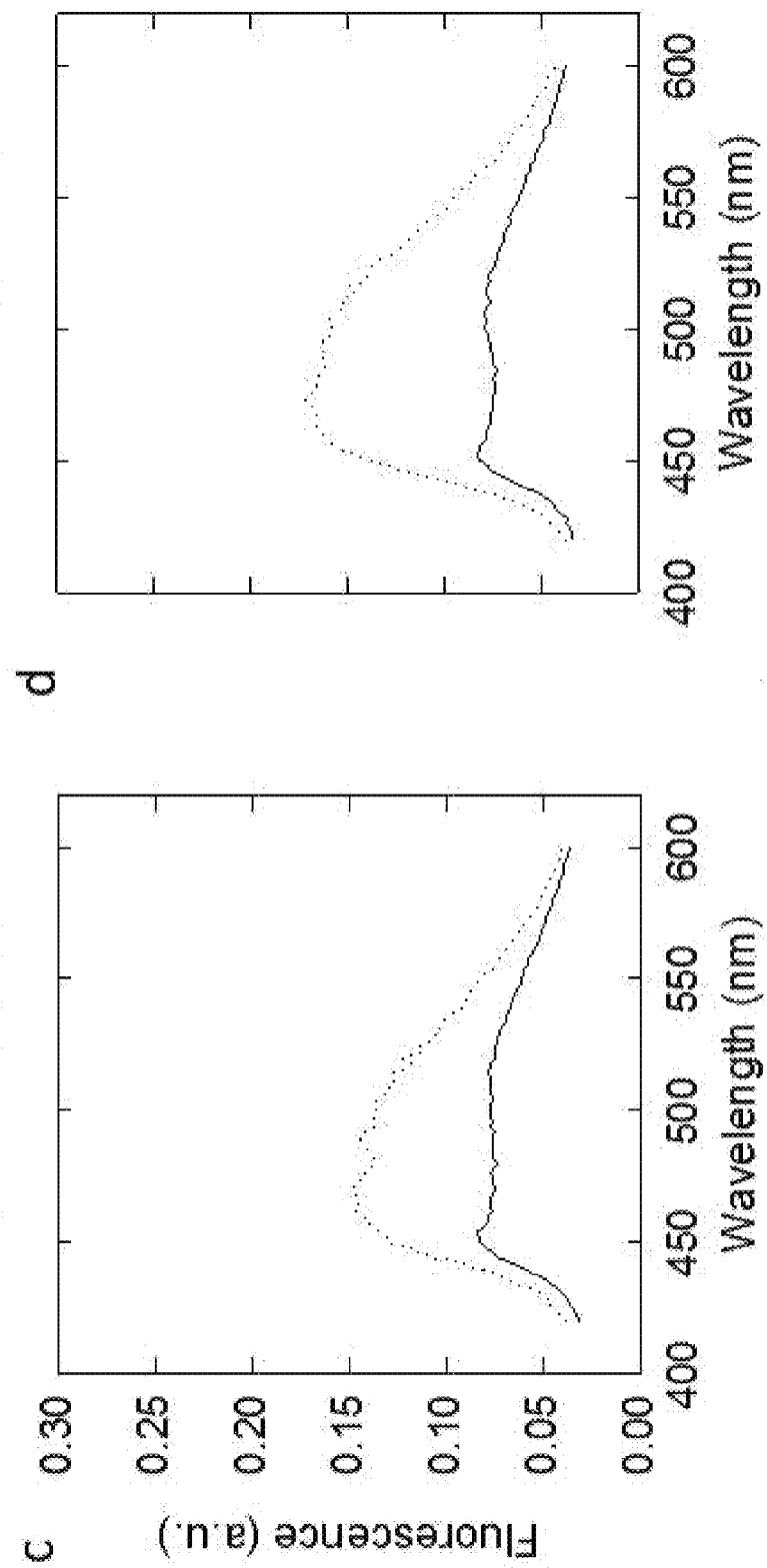
Figure 4c-d

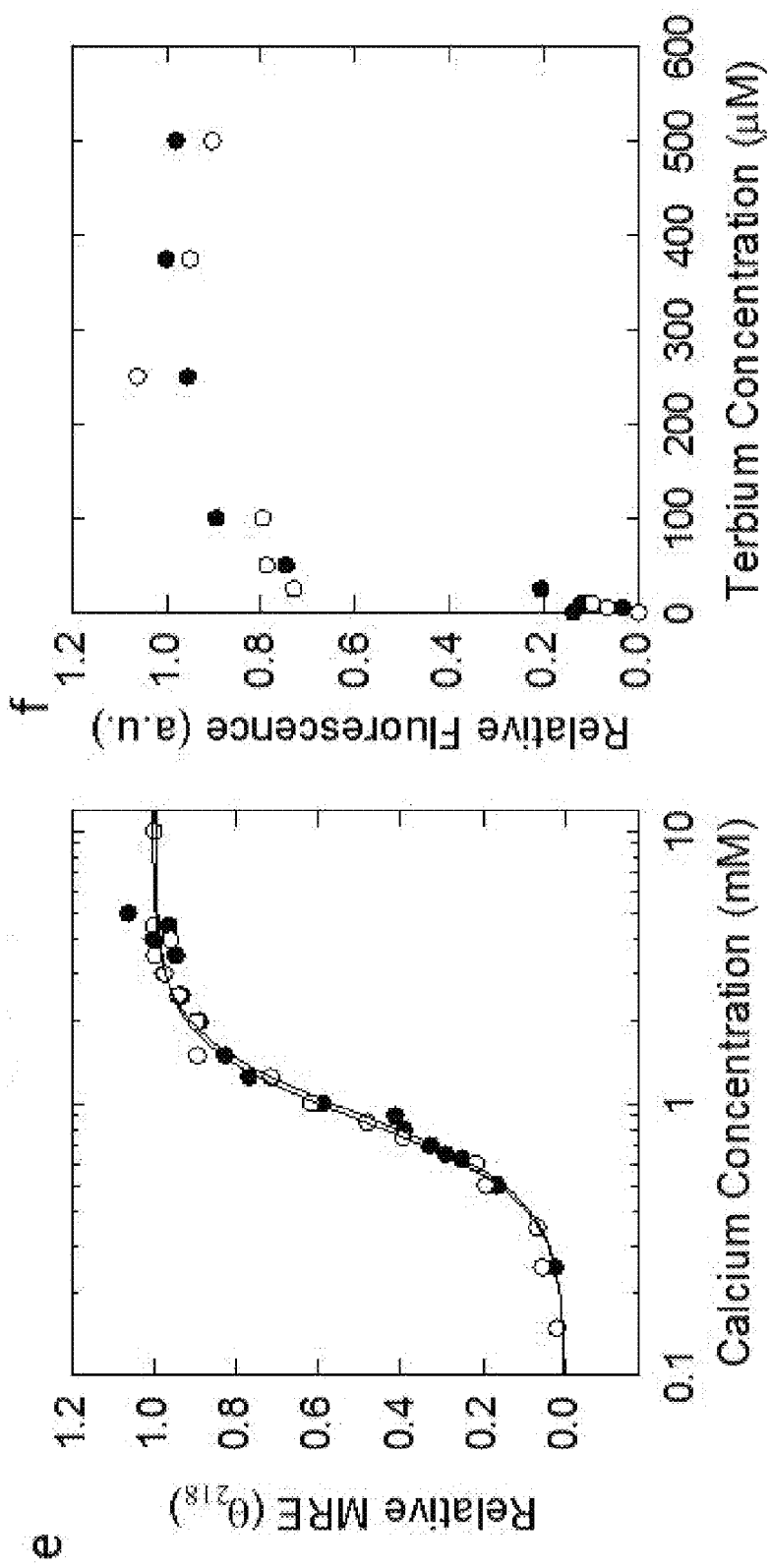
Figure 4e-f

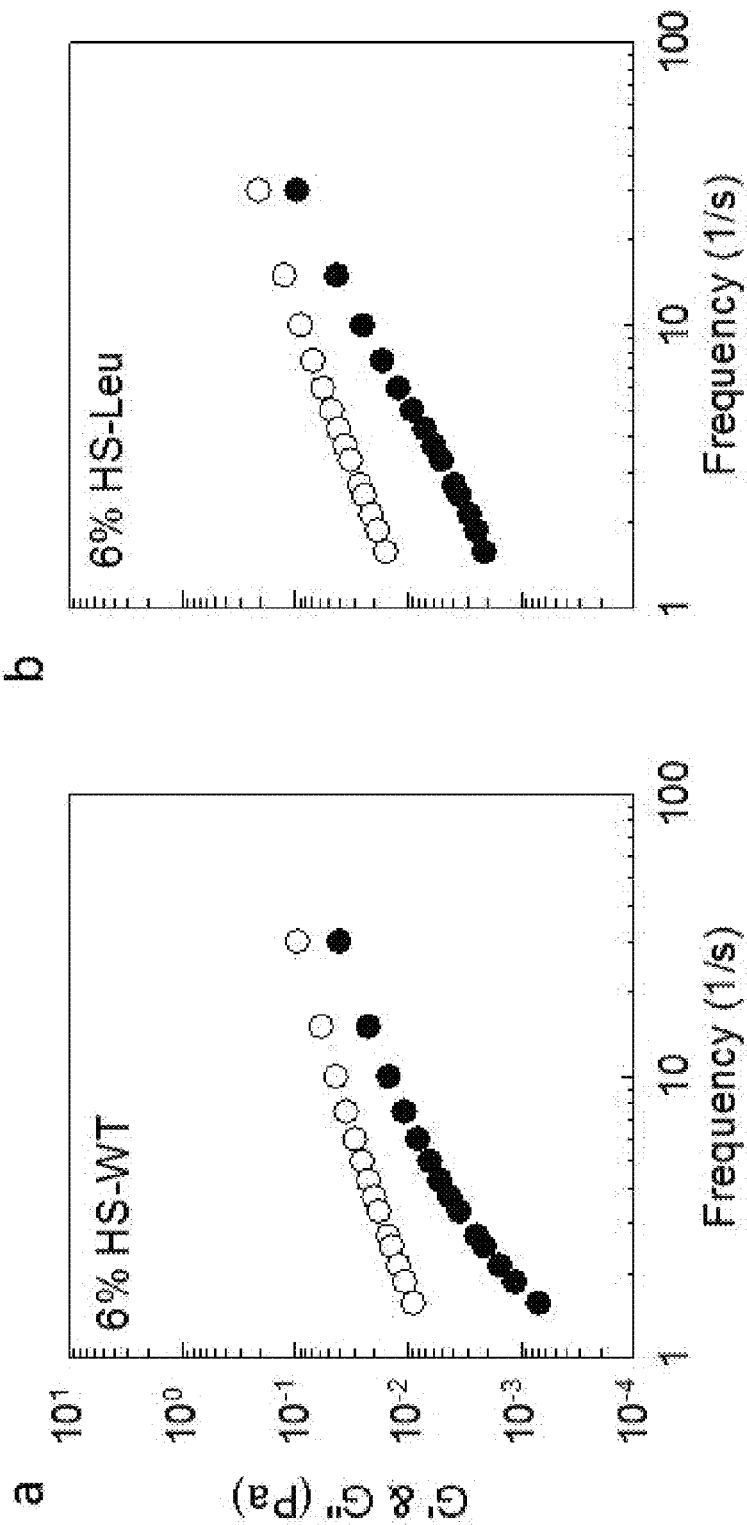
Figure 6a-b

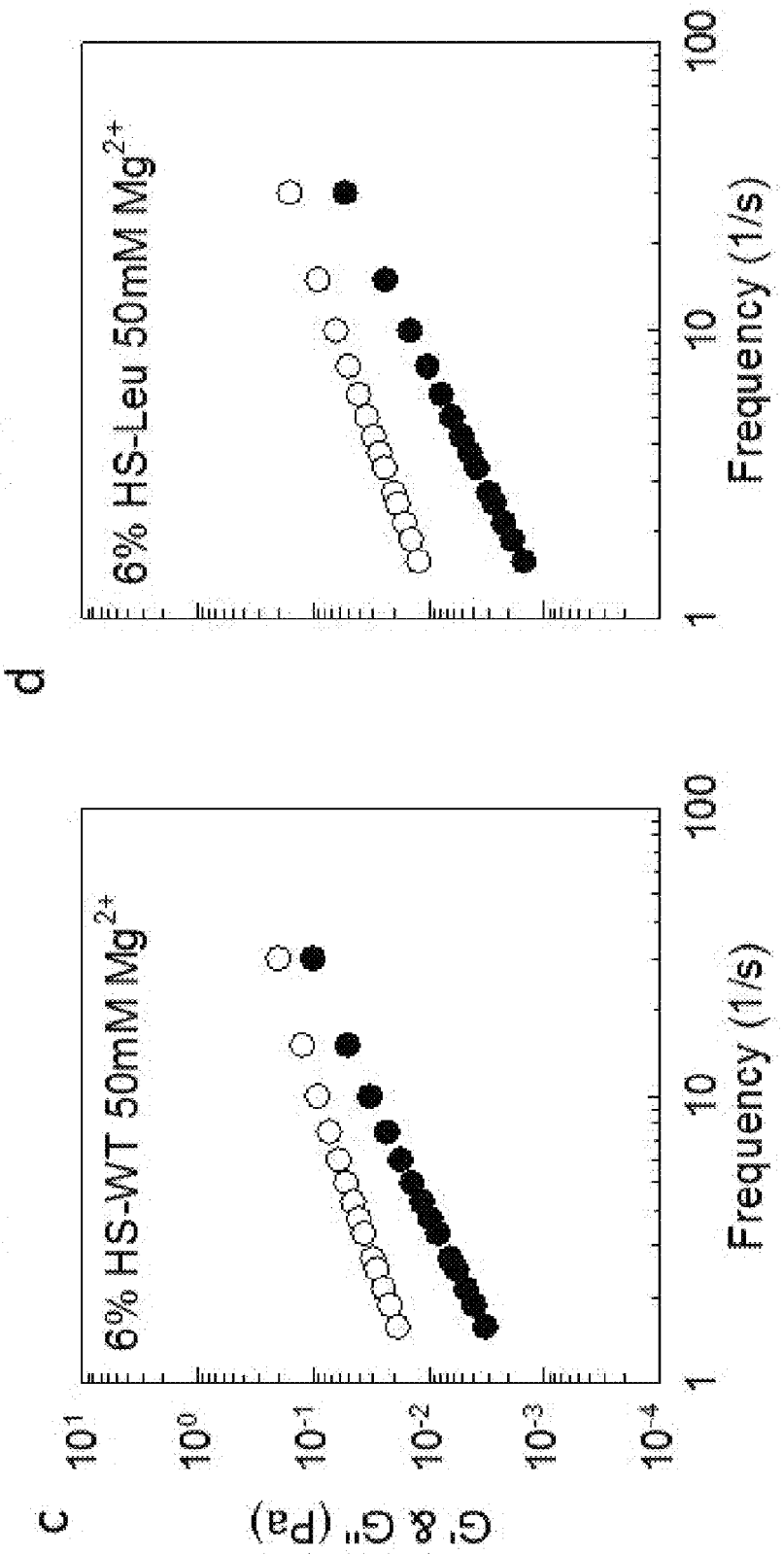
Figure 6c-d

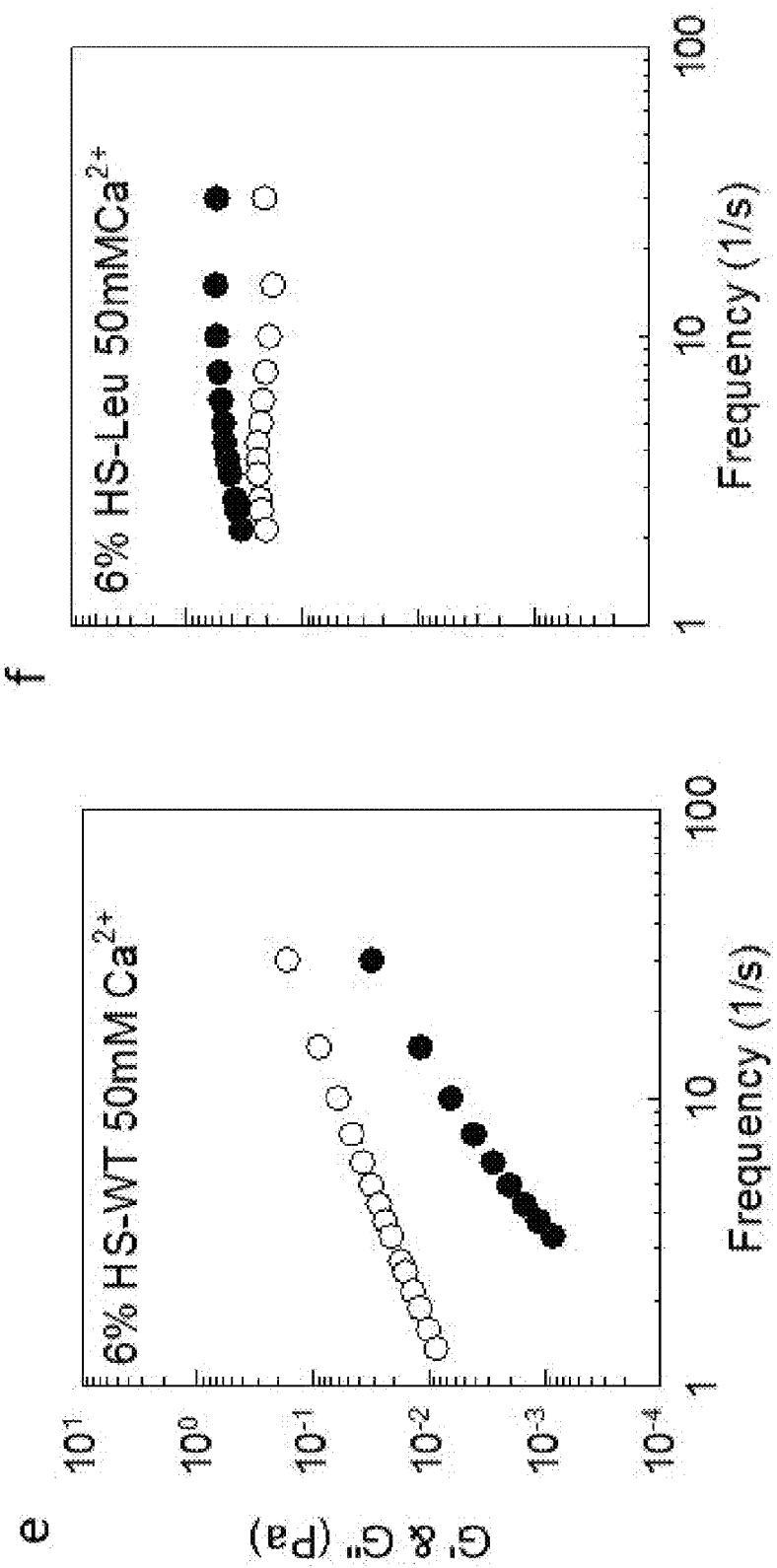
Figure 6e-f

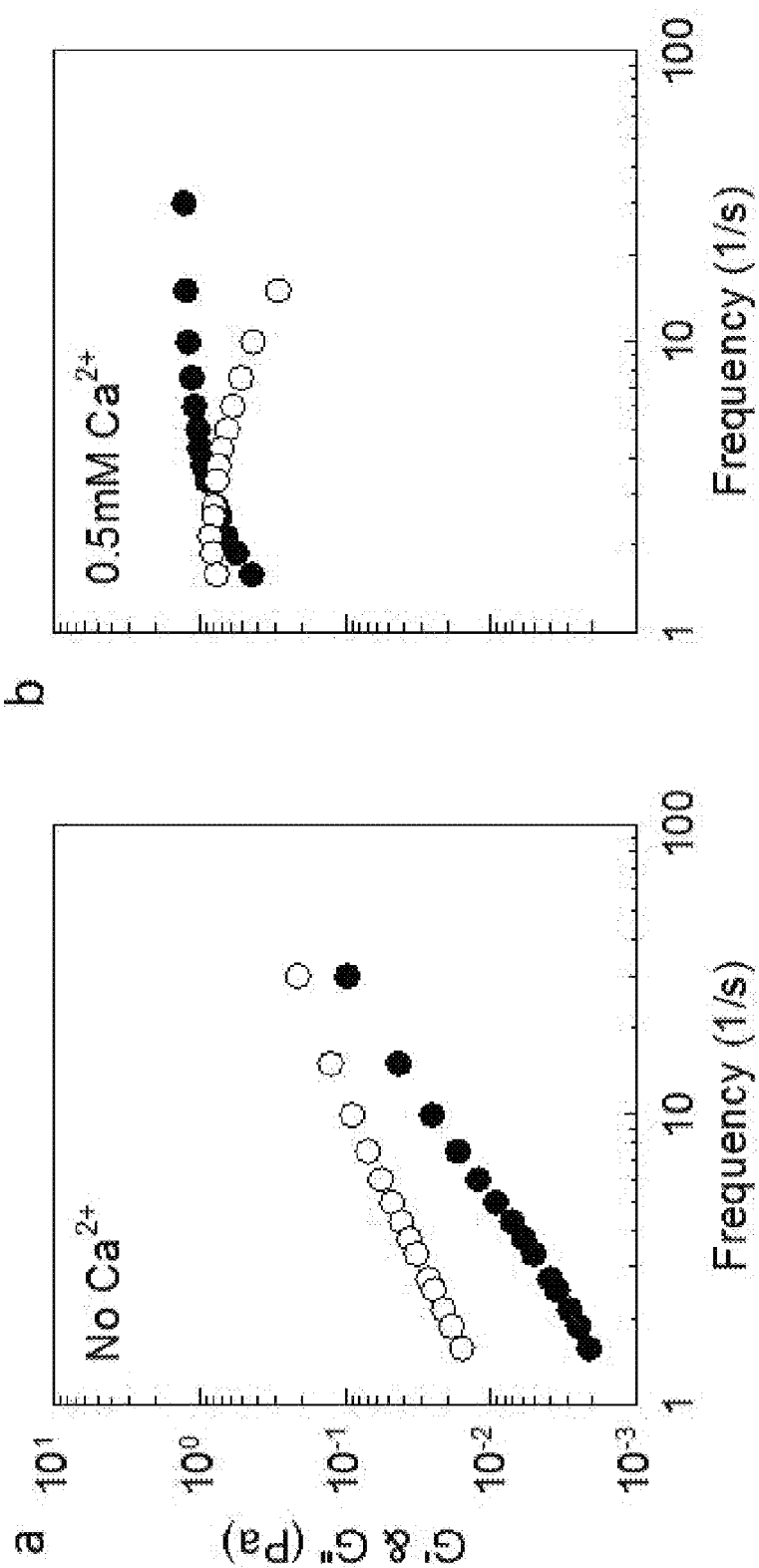
Figure 7a-b

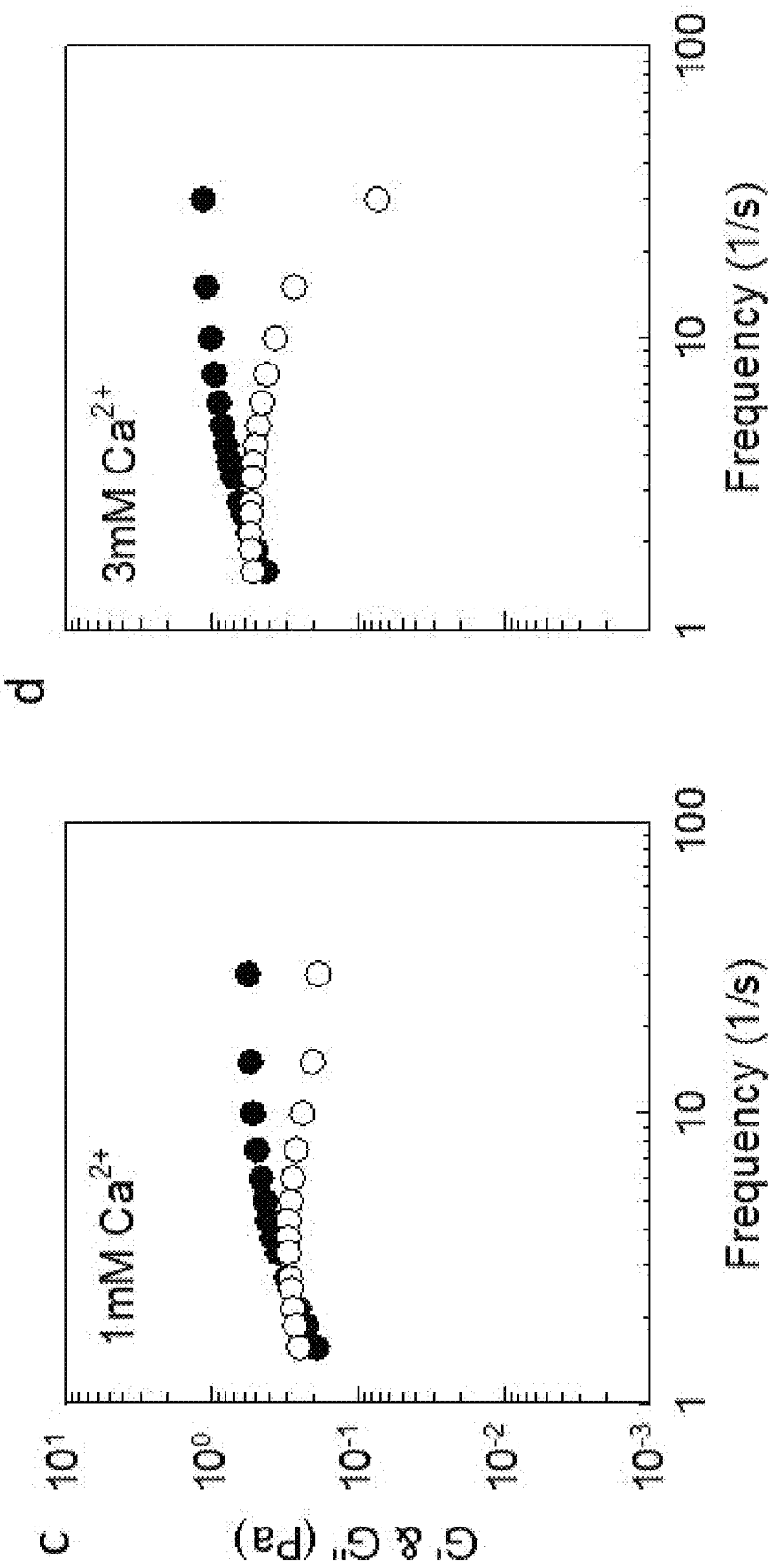
Figure 7c-d

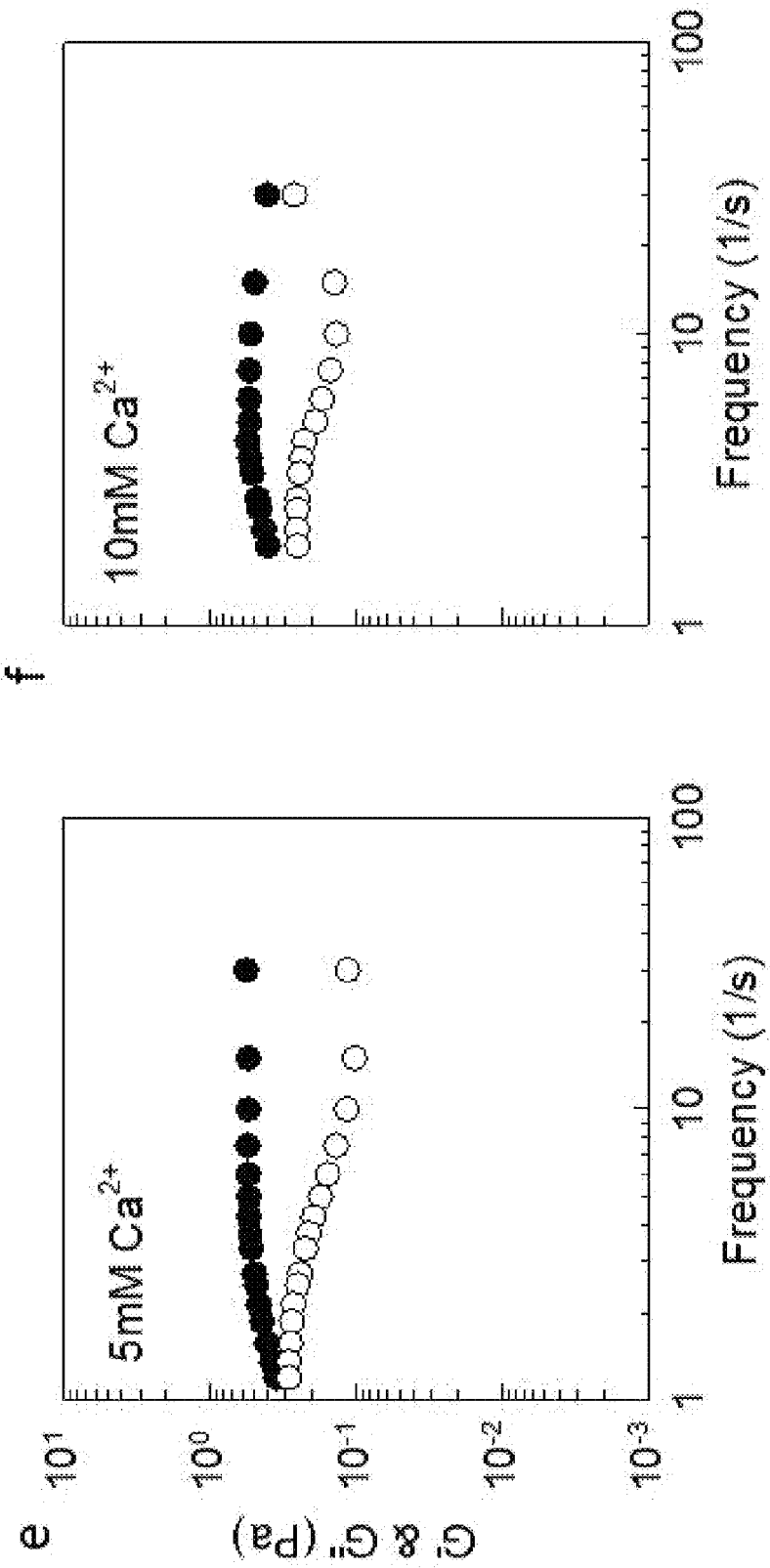
Figure 7e-f

SEQUENCE LISTING

```
<160> NUMBER OF SEQ ID NOS: 29

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Ala Arg Asp Asp Val Leu Ile
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Gly Asp Ala Gly Ala Asn Leu Leu Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Leu Ala Gly Asn Asp Val Leu Ser
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ala Gly Asp Asp Leu Leu Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Asp Glu Gly Ser Asp Leu Leu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asp Ala Gly Asn Asp Leu Leu Leu
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gln Gly Asp Asp Thr Tyr Leu Phe Gly
1               5                   10

<210> SEQ ID NO 8
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 8

Val Gly Tyr Gly His Asp Leu Ile Leu Glu
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gly Gly Gly His Asp Thr Ile Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 10

Xaa Xaa Xaa Xaa Xaa Xaa Xaa Xaa Xaa
1               5

<210> SEQ ID NO 11
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 11

Gly Xaa Xaa Xaa Xaa Xaa Xaa Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
```

```
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 12

Xaa Xaa Xaa Gly Xaa Xaa Xaa Xaa Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 13

Xaa Xaa Xaa Xaa Xaa Asp Xaa Xaa Xaa
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
```

```
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 14

Xaa Xaa Xaa Xaa Xaa Xaa Xaa Leu Xaa
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 15

Gly Xaa Xaa Gly Xaa Xaa Xaa Xaa Xaa
1               5

<210> SEQ ID NO 16
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 16

Gly Xaa Xaa Xaa Xaa Asp Xaa Xaa Xaa
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 17
```

-continued

```
Gly Xaa Xaa Xaa Xaa Xaa Xaa Leu Xaa
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 18

Xaa Xaa Xaa Gly Xaa Asp Xaa Xaa Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
```

```
<221> NAME/KEY: MOD_RES
<222> LOCATION: (6)..(6)
<223> OTHER INFORMATION: Aspartic acid or Asparagine

<400> SEQUENCE: 19

Xaa Xaa Xaa Xaa Xaa Xaa Leu Leu Leu
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine
<220> FEATURE:
<221> NAME/KEY: MOD_RES
<222> LOCATION: (10)..(10)
<223> OTHER INFORMATION: Phenylalanine or Glutamic acid

<400> SEQUENCE: 20

Xaa Xaa Xaa Xaa Xaa Xaa Xaa Xaa Xaa Xaa
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
```

```
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (10)..(10)
<223> OTHER INFORMATION: Phenylalanine or Glutamic acid

<400> SEQUENCE: 21

Xaa Gly Xaa Xaa Xaa Asp Xaa Xaa Leu Xaa
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine
<220> FEATURE:
<221> NAME/KEY: MOD_RES
<222> LOCATION: (10)..(10)
```

<223> OTHER INFORMATION: Phenylalanine or Glutamic acid

<400> SEQUENCE: 22

Xaa Xaa Xaa Xaa Xaa Xaa Xaa Xaa Xaa Xaa Gly
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 23

Xaa Xaa Xaa Xaa Xaa Xaa Xaa Xaa Xaa Glu
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or

```
            Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (6)..(6)
<223> OTHER INFORMATION: Aspartic acid or Asparagine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 24

Xaa Xaa Xaa Xaa Xaa Xaa Xaa Xaa Xaa Phe Gly
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycine, Valine or Serine
<220> FEATURE:
<221> NAME/KEY: MOD_RES
<222> LOCATION: (2)..(2)
<223> OTHER INFORMATION: Glycine, Serine, Aspartic acid or Leucine
<220> FEATURE:
<221> NAME/KEY: MOD_RES
<222> LOCATION: (3)..(3)
<223> OTHER INFORMATION: Alanine, Glutamic acid, Glutamine, Tyrosine or
      Glycine
<220> FEATURE:
<221> NAME/KEY: MOD_RES
<222> LOCATION: (4)..(4)
<223> OTHER INFORMATION: Glycine or Arginine
<220> FEATURE:
<221> NAME/KEY: MOD_RES
<222> LOCATION: (5)..(5)
<223> OTHER INFORMATION: Aspartic acid, Alanine, Asparagine, Serine or
      Histidine
<220> FEATURE:
<221> NAME/KEY: MOD_RES
<222> LOCATION: (7)..(7)
<223> OTHER INFORMATION: Valine, Leucine or Threonine
<220> FEATURE:
<221> NAME/KEY: MOD_RES
<222> LOCATION: (8)..(8)
<223> OTHER INFORMATION: Leucine, Isoleucine or Tyrosine
<220> FEATURE:
<221> NAME/KEY: MOD_RES
<222> LOCATION: (9)..(9)
<223> OTHER INFORMATION: Isoleucine, Leucine, Serine or Arginine

<400> SEQUENCE: 25

Xaa Xaa Xaa Xaa Xaa Asp Xaa Xaa Xaa
1               5
```

```
<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Asp Ala Gly Ala Asn Val Leu Asn
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Ala Gly Asp Asp Val Leu Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Asp Ala Gly Asn Asp Asp Leu Phe
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Gly Tyr Gly His Asp Thr Ile Tyr Glu
1               5                   10
```

LEUCINE BETA ROLL DOMAINS AND USES THEREOF

This application claims benefit of priority to U.S. Provisional Patent Application No. 61/558,826, filed Nov. 11, 2011, the entire disclosure of which is hereby incorporated by reference herein.

STATEMENT OF GOVERNMENT SUPPORT

This invention was made with government support under grant number FA9550-06-1-0264 awarded by AFOSR MURI. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

SEQUENCE LISTING

The instant application contains a Sequence Listing which has been submitted in ASCII format via EFS-Web and is hereby incorporated by reference in its entirety. Said ASCII copy, created on Jan. 14, 2013, is named 19240966.txt and is 17,871 bytes in size.

BACKGROUND OF THE INVENTION

Current work in the development of smart materials and hydrogels has opened the door to a host of potential applications in such fields as drug delivery, tissue engineering and microfluidics. Hydrogels are composed of water soluble monomers which are physically or covalently cross-linked to form three dimensional polymer networks. This cross-linking can often times be controlled by the incorporation of stimulus responsive proteins or peptides into the monomeric building block. Stimuli such as pH, temperature or ionic strength can be used to induce changes which can regulate the assembly of hydrogel networks. Examples of protein domains which facilitate environmentally cued gelation include elastin-like peptides, calmodulin, and α-helical leucine zipper domains.

Helical leucine zippers are a structural motif found in DNA binding proteins. The name is derived from the periodic repeat of leucine residues. These hydrophobic amino acids protrude outward and run down a plane of the helix. This creates a hydrophobic driving force which leads to the formation of "zipped" coiled-coil bundles. These domains have been extensively characterized in the literature proving to be beneficial for creating stimulus responsive hydrogel networks as they assemble and dissociate in response to changes in temperature and pH. These domains have been appended to enzymes and other proteins to create functionalized hydrogel constructs.

There is a need for stimulus-responsive hydrogels in which cross-linking can be allosterically controlled. This invention addresses these needs.

SUMMARY OF THE INVENTION

In one aspect, the invention relates to a protein hydrogel network comprising a polypeptide beta roll, a leucine zipper and a soluble linker region. In some embodiments, the beta roll is fused to a leucine zipper with a soluble linker region. In some embodiments, the polypeptide beta roll comprises a scaffold from the RTX domain of adenylate cyclase, wherein leucine mutations are introduced on the beta roll domain. In some embodiments, the beta roll domain comprises the amino acid sequence $X_1X_2X_3X_4X_5X_6X_7X_8X_9$ (SEQ ID NO: 10), wherein (a) $X_1$ is an amino acid selected from the group consisting of glycine, valine and serine;

(b) $X_2$ is an amino acid selected from the group consisting of glycine, serine, aspartic acid and leucine;

(c) $X_3$ is an amino acid selected from the group consisting of alanine, glutamic acid, glutamine, tyrosine and glycine;

(d) $X_4$ is an amino acid selected from the group consisting of glycine and arginine;

(e) $X_5$ is an amino acid selected from the group consisting of aspartic acid, alanine, asparagine, serine, and histidine;

(f) $X_6$ is an amino acid selected from the group consisting of aspartic acid and asparagine;

(g) $X_7$ is an amino acid selected from the group consisting of valine, leucine, and threonine;

(h) $X_8$ is an amino acid selected from the group consisting of leucine, isoleucine, and tyrosine; and (i) $X_9$ is an amino acid selected from the group consisting of isoleucine, leucine, serine, and arginine.

In some embodiments, the amino acid sequence is GSARDDVLI (SEQ ID NO: 1), GDAGANLLL (SEQ ID NO: 2), GLAGNDVLS (SEQ ID NO: 3), GGAGDDLLL (SEQ ID NO: 4), GDEGSDLLS (SEQ ID NO: 5), GDAGNDLLL (SEQ ID NO: 6), GGQGDDTYLFG SEQ ID NO: 7), VGYGHDLILE (SEQ ID NO: 8), or SGGGHDTIR (SEQ ID NO: 9). In some embodiments, the amino acid sequence is GDAGANLLL (SEQ ID NO: 2), GGAGDDLLL (SEQ ID NO: 4), GDAGNDLLL (SEQ ID NO: 6), or VGYGHDLILE (SEQ ID NO: 8).

In one aspect of the invention, an α-helical leucine zipper domain fused to the leucine rich beta roll peptide forms a hydrogel by physical cross-linking in calcium rich environments.

BRIEF DESCRIPTION OF THE FIGURES

The patent or application file contains at least one drawing executed in color. Copies of this patent or patent application publication with color drawing(s) will be provided by the Office upon request and payment of the necessary fee.

The following figures are illustrative only and are not intended to be limiting.

FIG. 4 shows WT and leucine beta roll calcium responsiveness and characterization. (a) WT and (b) leucine beta roll CD spectra in the presence (•••) and absence (—) of 50 mM calcium showing similar responses. These results are consistent with bis-ANS binding results for WT and leucine beta rolls shown in (c) and (d), respectively. The higher bis-ANS signal observed for the leucine construct is due to the increased number of nonpolar residues. The CD calcium titration (e) shows nearly identical curves for both WT (•) and leucine (○) beta roll proteins. The data are fit to the Hill equation. Terbium binding results are shown in (f) for the WT (•) and leucine (○) constructs. Both show very similar responses.

FIG. 6 shows HS-WT and HS-leucine beta roll microrheology. Elastic (•) and viscous (○) moduli have been calculated for 6 wt % HS-WT and HS-leucine beta roll samples. (a) HS-WT and (b) HS-leucine remain viscous in buffer, (c) HS-WT and (d) HS-leucine show no response to magnesium. The HS-WT beta roll remains a viscous liquid with the addition of calcium (e), whereas there is a clear shift in the mechanical properties of HS-leucine beta roll upon addition of calcium (f), gaining elasticity as compared with the HS-WT control.

FIG. 7 shows HS-leucine beta roll calcium titration and the transition from viscous liquid to hydrogel. Elastic (•) and viscous (○) moduli have been calculated for 6 wt % HS-leucine beta roll samples (a) in the absence of calcium, (b) at 0.5 mM calcium, (c) at 1 mM calcium, (d) at 3 mM calcium, (e) at 5 mM calcium and (f) at 10 mM calcium.

DETAILED DESCRIPTION OF THE INVENTION

Figure 1:
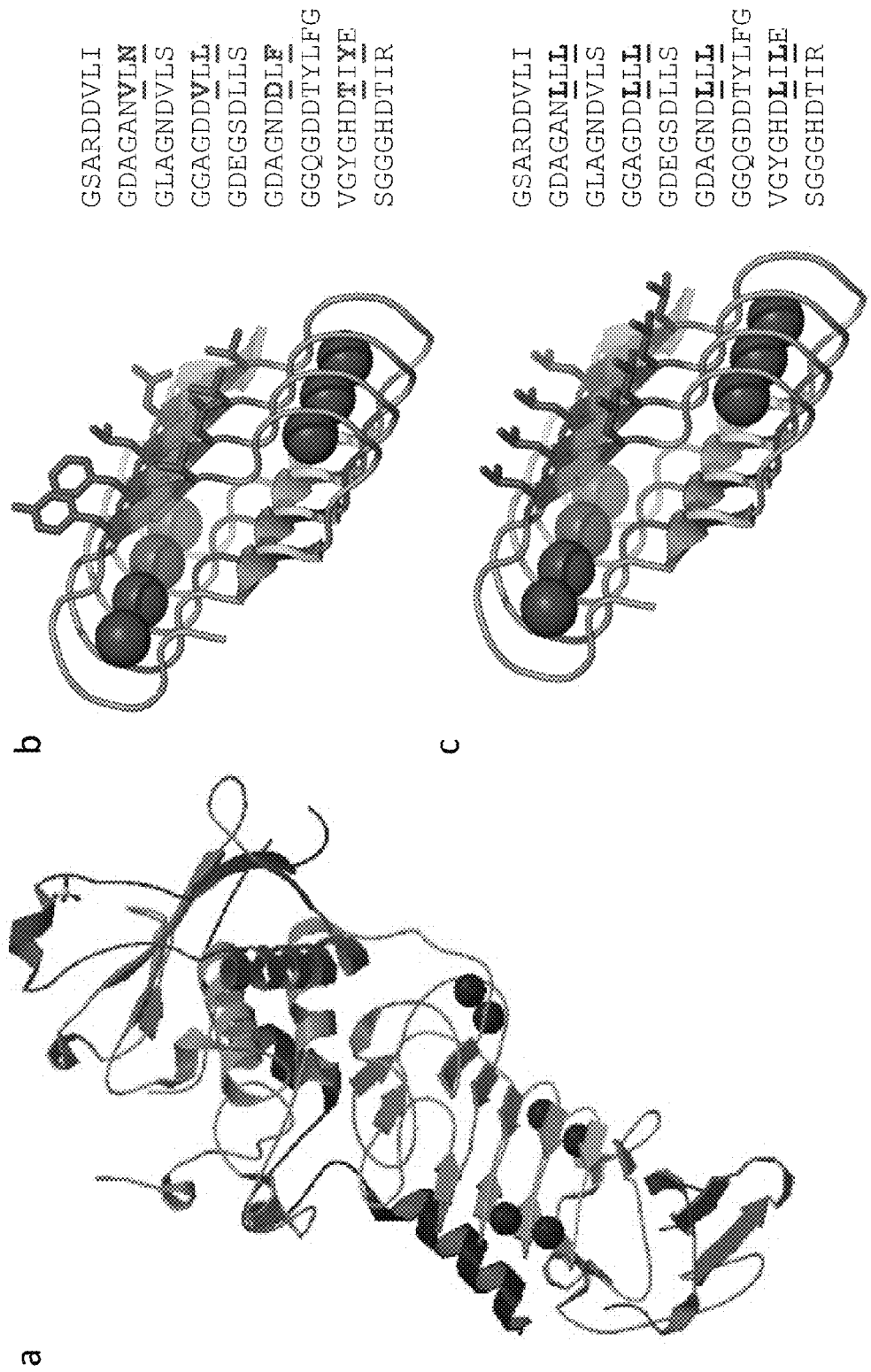
FIG. 1 shows beta roll structures: (a) Crystal structure of alkaline phosphatase from *Pseudomonas* TAC II 18 (PDB 1OOQ). The folded beta roll domain can been seen in the lower half with the bound calcium ions in grey. The known structure of this folded beta roll was used to model the WT and leucine adenylate cyclase beta roll domains. The crystal structure of adenylate cyclase from *B. Pertussis* has not been solved (b) Model of the WT adenylate cyclase beta roll with sequence. Here, the surface exposed residues in the folded conformation are highlighted in magenta with the residues underlined in the sequence. Calcium ions are shown in red. (c) Model of the mutant leucine beta roll with sequence. The leucine mutations to the WT beta roll are shown in blue and underlined in the sequence. Figure discloses SEQ ID NOS 1, 26, 3, 27, 5, 28, 7, 29, 9, and 1-9, respectively, in order of appearance.

The issued patents, applications, and other publications that are cited herein are hereby incorporated by reference to the same extent as if each was specifically and individually indicated to be incorporated by reference.

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

In one aspect, the invention relates to a protein hydrogel network comprising a polypeptide beta roll, a leucine zipper and a soluble linker region. In some embodiments, the beta roll is fused to a leucine zipper with a soluble linker region. In some embodiments, the polypeptide beta roll comprises a scaffold from the RTX domain of adenylate cyclase, wherein leucine mutations are introduced on the beta roll domain.

In some embodiments, the beta roll domain comprises the amino acid sequence $X_1X_2X_3X_4X_5X_6X_7X_8X_9$ (SEQ ID NO: 10), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 10), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 11), wherein
(a) $X_1$ is the amino acid glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;

(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 11), wherein
(a) $X_1$ is the amino acid glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 12), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is the amino acid glycine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 12), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is the amino acid glycine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 13), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is the amino acid aspartic acid;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 13), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is the amino acid aspartic acid;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 14), wherein
(a) $X_1$ is an amino acid selected from the group consisting of glycine, valine, and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is the amino acid leucine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 14), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is the amino acid leucine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 15), wherein
(a) $X_1$ is the amino acid glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is the amino acid glycine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 15), wherein
(a) $X_1$ is the amino acid glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is the amino acid glycine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 16), wherein
(a) $X_1$ is the amino acid selected glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is the amino acid aspartic acid;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 16), wherein
(a) $X_1$ is the amino acid selected glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is the amino acid aspartic acid;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 17), wherein
(a) $X_1$ is the amino acid glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is the amino acid leucine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 17), wherein
(a) $X_1$ is the amino acid glycine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is the amino acid leucine; and (i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 18), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is the amino acid glycine;
(e) $X_5$ is an amino acid selected from the group consisting of aspartic acid, alanine, asparagine, serine, and histidine;
(f) $X_6$ is the amino acid aspartic acid;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain consists essentially of the amino acid sequence $X_1X_2X_3X_4X_5X_6X_7X_8X_9$ (SEQ ID NO: 18), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is the amino acid glycine;
(e) $X_5$ is an amino acid selected from the group consisting of aspartic acid, alanine, asparagine, serine, and histidine;
(f) $X_6$ is the amino acid aspartic acid;
(g) $X_7$ is an amino acid selected from the group consisting of valine, leucine, and threonine;
(h) $X_8$ is an amino acid selected from the group consisting of leucine, isoleucine, and tyrosine; and
(i) $X_9$ is an amino acid selected from the group consisting of isoleucine, leucine, serine, and arginine.

In some embodiments, the beta roll domain comprises the amino acid sequence $X_1X_2X_3X_4X_5X_6X_7X_8X_9$ (SEQ ID NO: 19), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is the amino acid leucine;
(h) $X_8$ is the amino acid leucine; and
(i) $X_9$ is the amino acid leucine.

In some embodiments, the beta roll domain consists essentially of the amino acid sequence $X_1X_2X_3X_4X_5X_6X_7X_8X_9$ (SEQ ID NO: 19), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is the amino acid leucine;
(h) $X_8$ is the amino acid leucine; and
(i) $X_9$ is the amino acid leucine.

In some embodiments, the beta roll domain comprises the amino acid sequence $X_1X_2X_3X_4X_5X_6X_7X_8X_9X_{10}$ (SEQ ID NO: 20), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine;
(i) $X_9$ is an amino acid selected from the group consisting of isoleucine, leucine, serine, and arginine; and
(j) $X_{10}$ is an amino acid selected from the group consisting of phenylalanine and glutamic acid.

In some embodiments, the beta roll domain consists essentially of the amino acid sequence $X_1X_2X_3X_4X_5X_6X_7X_8X_9X_{10}$ (SEQ ID NO: 20), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine;
(i) $X_9$ is an amino acid selected from the group consisting of isoleucine, leucine, serine, and arginine; and
(j) $X_{10}$ is an amino acid selected from the group consisting of phenylalanine and glutamic acid.

In some embodiments, the beta roll domain comprises the amino acid sequence $X_1X_2X_3X_4X_5X_6X_7X_8X_9X_{10}$ (SEQ ID NO: 21), wherein
(a) $X_1$ is an amino acid selected from the group consisting of glycine, valine and serine;
(b) $X_2$ comprises the amino acid glycine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;

(f) $X_6$ is aspartic acid;
(g) $X_7$ is an amino acid selected from the group consisting of valine, leucine, and threonine;
(h) $X_8$ is an amino acid selected from the group consisting of leucine, isoleucine, and tyrosine;
(i) $X_9$ is the amino acid selected from the group consisting of leucine; and
(j) $X_{10}$ is an amino acid selected from the group consisting of phenylalanine and glutamic acid.

In some embodiments, the beta roll domain consists essentially of the amino acid sequence $X_1X_2X_3X_4X_5X_6X_7X_8X_9X_{10}$ (SEQ ID NO: 21), wherein
(a) $X_1$ is an amino acid selected from the group consisting of glycine, valine and serine;
(b) $X_2$ comprises the amino acid glycine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is aspartic acid;
(g) $X_7$ is an amino acid selected from the group consisting of valine, leucine, and threonine;
(h) $X_8$ is an amino acid selected from the group consisting of leucine, isoleucine, and tyrosine;
(i) $X_9$ is the amino acid selected from the group consisting of leucine; and
(j) $X_{10}$ is an amino acid selected from the group consisting of phenylalanine and glutamic acid.

In some embodiments, the beta roll domain comprises the amino acid sequence $X_1X_2X_3X_4X_5X_6X_7X_8X_9X_{10}X_{11}$ (SEQ ID NO: 22), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine;
(i) $X_9$ is an amino acid selected from the group consisting of isoleucine, leucine, serine, and arginine;
(j) $X_{10}$ is an amino acid selected from the group consisting of phenylalanine and glutamic acid; and
(k) $X_{11}$ is the amino acid glycine.

In some embodiments, the beta roll domain consists essentially of the amino acid sequence $X_1X_2X_3X_4X_5X_6X_7X_8X_9X_{10}X_{11}$ (SEQ ID NO: 22), wherein
(a) $X_1$ is an amino acid selected from the group consisting of glycine, valine and serine;
(b) $X_2$ is an amino acid selected from the group consisting of glycine, serine, aspartic acid and leucine;
(c) $X_3$ is an amino acid selected from the group consisting of alanine, glutamic acid, glutamine, tyrosine and glycine;
(d) $X_4$ is an amino acid selected from the group consisting of glycine and arginine;
(e) $X_5$ is an amino acid selected from the group consisting of aspartic acid, alanine, asparagine, serine, and histidine;
(f) $X_6$ is an amino acid selected from the group consisting of aspartic acid and asparagine;
(g) $X_7$ is an amino acid selected from the group consisting of valine, leucine, and threonine;
(h) $X_8$ is an amino acid selected from the group consisting of leucine, isoleucine, and tyrosine;
(i) $X_9$ is an amino acid selected from the group consisting of isoleucine, leucine, serine, and arginine;
(j) $X_{10}$ is an amino acid selected from the group consisting of phenylalanine and glutamic acid; and
(k) $X_{11}$ is the amino acid glycine.

In some embodiments, the beta roll domain comprises amino acid sequence selected from GSARDDVLI (SEQ ID NO:1), GDAGANLLL (SEQ ID NO:2), GLAGNDVLS (SEQ ID NO:3), GGAGDDLLL (SEQ ID NO:4), GDEGSDLLS (SEQ ID NO:5), GDAGNDLLL (SEQ ID NO:6), GGQGDDTYLFG (SEQ ID NO:7), VGYGHDLILE (SEQ ID NO:8), and SGGGHDTIR (SEQ ID NO:9).

In some embodiments, the amino acid sequence is selected from GSARDDVLI (SEQ ID NO:1), GDAGANLLL (SEQ ID NO:2), GLAGNDVLS (SEQ ID NO:3), GGAGDDLLL (SEQ ID NO:4), GDEGSDLLS (SEQ ID NO:5), GDAGNDLLL (SEQ ID NO:6), GGQGDDTYLFG (SEQ ID NO:7), VGYGHDLILE (SEQ ID NO:8), and SGGGHDTIR (SEQ ID NO:9).

In some embodiments, the amino acid sequence comprises GDAGANLLL (SEQ ID NO: 2), GGAGDDLLL (SEQ ID NO: 4), GDAGNDLLL (SEQ ID NO: 6), or VGYGHDLILE (SEQ ID NO: 8)

In some embodiments, the amino acid sequence consists essentially of GDAGANLLL (SEQ ID NO: 2), GGAGDDLLL (SEQ ID NO: 4), GDAGNDLLL (SEQ ID NO: 6), or VGYGHDLILE (SEQ ID NO: 8).

In some embodiments, the amino acid sequence is GSARDDVLI (SEQ ID NO:1).

In some embodiments, the amino acid sequence is GDAGANLLL (SEQ ID NO:2).

In some embodiments, the amino acid sequence is GLAGNDVLS (SEQ ID NO:3).

In some embodiments, the amino acid sequence is GGAGDDLLL (SEQ ID NO:4).

In some embodiments, the amino acid sequence is GDEGSDLLS (SEQ ID NO:5).

In some embodiments, the amino acid sequence is GDAGNDLLL (SEQ ID NO:6).

In some embodiments, the amino acid sequence is GGQGDDTYLFG (SEQ ID NO:7).

In some embodiments, the amino acid sequence is VGYGHDLILE (SEQ ID NO:8).

In some embodiments, the amino acid sequence is SGGGHDTIR (SEQ ID NO:9).

In one aspect of the invention, an α-helical leucine zipper domain fused to the leucine rich beta roll peptide forms a hydrogel by physical cross-linking in calcium rich environments.

Self-assembling hydrogels are highly versatile materials with applications in biosensors, chemical catalysis, tissue engineering, and drug delivery. In particular, the ability of a gel to reversibly assemble in response to a stimulus such as the presence of a certain chemical or compound is a highly desired property. In some embodiments, technology utilizes the induced folding of an engineered protein to trigger crosslinking and hydrogel formation. The modular design allows the incorporation of additional elements in the hydrogel, enabling hydrogel formation in situ of any given protein or enzyme.

Hydrogels are low-density cross-linked polymers that can hold many times their weight in water. Reversible hydrogel formation can be achieved by triggering non-covalent crosslinking of polymers such as proteins. Exemplary hydrogels are described, for example in U.S. Pat. Nos. 7,625,951; 7,179,487; Nature Materials 2005, 4, 298-302; Langmuir 2012, 28 (4), 2269-2274; and J Mater Sci: Mater Med 2011, 22:2651-2657; each herein incorporated by reference in its entirety.

The beta-roll motif is a protein structure that folds upon specific binding of calcium ions. Reduction of calcium concentration induces reversible unfolding of the beta-roll. Herein, modified beta-roll proteins that incorporate a leucine rich exterior are described. This construct was fused with an alpha-helical leucine-zipper domain derived from a native transcription factor.

Micro-rheology data demonstrate that in the absence of calcium, a concentrated solution of the peptide is a viscous liquid, presumably because the engineered beta-roll sequence has not folded and therefore does not cross-link. However, when calcium is added, concentrated peptide solutions exhibit rheological behavior indicative of a hydrogel. When combined with other cross-linking domains, this allows for allosterically controlled protein hydrogel formation. The hydrogels themselves, for example, find utility where it would be useful to deposit a gel as a viscous liquid, and then cross-link it in place through the addition of calcium. Additional applications include tissue engineering and bioelectrocatalysis, and other biotechnologies. The technology can also serve as a platform for many different applications, including but not limited to biosensors, bioengineering, tissue replacement, wound dressing, drug delivery, microfluidics and bio (electro)catalysis.

A significant advantage over similar technologies is that the hydrogels herein are completely protein based, ensuring biocompatibility and degradability, and reducing risk of toxicity.

Another advantage is the ability of calcium to trigger hydrogel formation among soluble proteins, vastly increasing possible applications due to ease of delivery. For instance, in microfluidics or biosensor applications, a protein containing liquid could be injected and transported to an appropriate site, after which calcium addition could solidify the gel. This would change the viscosity and rheology of the material, thus enabling trapping of other species in the device.

In addition, the physical changes of the hydrogel itself could be utilized as a sensor for calcium concentration. Addition of other, perhaps enzymatic, components to the cross linking modules would enable catalytic applications where enzymes can be retained while a flow administers the substrate. If the scaffold is altered so that other ions or compounds trigger assembly then the versatility of the technology as a biosensor would be increased, and could perhaps be used in implants to monitor ion concentrations.

One way to create controllable cross-linking domains is to begin with an environmentally responsive peptide and modify it to create a hydrogel cross-link (Chockalingam, K. et al. *Protein Eng. Des. Sel.* 2007, 20, 155-161; herein incorporated by reference in its entirety). Protein hydrogels whose monomers contain helical leucine zippers are described, for example, in WO 2008/011204; herein incorporated by reference in its entirety. These hydrogels however self-assemble, accordingly there is a need for stimulus-responsive hydrogels in which cross-linking can be allosterically controlled. For example, the beta-roll domain is a right-handed beta helix found in several proteins such as, for example, the metalloprotease enzyme serralysin (Baumann, U. *J. Mol. Biol.* 1994, 242, 244-251; herein incorporated by reference in its entirety). The consensus sequence for the beta roll consists of tandem repeats of 9 amino acids, and each of these in turn binds a calcium atom. The domain is capable of reversibly unfolding upon removal of the calcium (Blenner, M. A. et al. *J. Mol. Biol.* 2010, 400, 244-256; Szilvay, G. R. et al. *Biochemistry* 2009, 48, 11273-11282; Ringler, P. et al. *Science* 2003, 302, 106-109; each herein incorporated by reference in its entirety). The radially protruding amino acids on the sides of the beta roll are mutated to leucine residues in order to create a leucine-zipper like interface.

Stimulus-responsive hydrogels are being increasingly developed for applications including drug delivery, tissue engineering and biosensors. Herein is described a peptide that forms a calcium-dependent hydrogel using a rationally engineered beta roll peptide. In the absence of calcium, the peptide is intrinsically disordered. Upon addition of calcium, the peptide forms a corkscrew-like structure. In some embodiments, a leucine zipper forming helical domain is added to the engineered beta roll and, in some embodiments, these constructs are able to form hydrogels by physical cross-linking in calcium rich environments. The structural properties of the mutant beta roll have been compared to the wild type by circular dichroism, 4,4'-dianilino-1,1'-binaphthyl-5,5'-disulfonic acid (bis-ANS) binding and terbium binding. The elastic and viscous moduli of the hydrogels have been measured at various calcium concentrations using a particle tracking technique.

The beta roll peptide domains described herein are a class of designed peptides which possess the ability to cross-link in the presence of calcium ions. Thus, the new domain is suitable for creating physical cross-links and a subsequent hydrogel network. A beta roll scaffold taken from the block V repeats-in-toxin (RTX) domain of adenylate cyclase from *Bordetella pertussis* is a modular repeat protein which has been shown to be intrinsically disordered in the absence of calcium. In calcium rich environments, the peptide forms a corkscrew like structure with two parallel beta sheet faces separated by calcium binding turns. A C-terminal capping group responsible for entropic stabilization is required for the calcium induced conformational response. The calcium responsiveness and capping requirements have been characterized previously. Each beta strand in the folded state contains two amino acids which are exposed to the solvent. Mutation of 8 of these residues to leucine surprisingly creates a hydrophobic face suitable for dimerization which is formed only after calcium binding (FIG. 1). The result is an allosteric mutant beta roll that allows for the formation of a dimerizing interface in the presence of calcium.

The RTX gene sequence can fold into a beta roll domain. The RTX sequences are repeating 9 amino acid sequences found in secreted proteins from pathogenic bacteria. Two of the repeats together form a full turn of the beta roll domain which adopts a corkscrew structure comprised of a turn followed by a short beta sheet followed by a turn. An aspartic acid residue in each turn binds calcium and the calcium atom sits between two consecutive turns of the beta roll domain. There are beta sheet structures on both sides of the corkscrew structure, and this causes two of the side chains in the sheet region to project radially outward on each face of the beta roll. Some of the fifth beta roll domain from the adenylate cyclase protein from *Bordetella pertussis* has also been characterized. This beta roll domain folds reversibly in the presence of calcium, and the domain is specific for calcium over other divalent cations. The capping requirements of the beta roll indicate that the beta roll requires a C-terminal capping domain in order to fold in response to calcium. The native capping domain confers high affinity for calcium, but other capping domains can be added which also enable calcium responsiveness. Without being bound by theory, these results suggest that the folding is stabilized through entropic rather than enthalpic contributions from the capping domain. Although the native beta roll domain has amino acids projecting from the core of the corkscrew, it does not appear that the domain has been evolved for biomolecular recognition or protein/protein interactions.

Herein, protein design to replace the 8 radially projecting amino acids on one face of the beta roll domain with leucine side chains is performed. The change appears to have no or minimal impact on the calcium induced conformational change of the beta roll domain as measured by circular dichroism. A new construct containing one of the leucine zipper alpha-helical appendages described followed by an unstructured soluble domain followed by the newly engineered beta roll domain is presented. Microrheology data demonstrate that in the absence of calcium, a concentrated solution of the peptide is a viscous liquid. Without being bound by theory, this may be due to the engineered RTX sequence not being folded into the beta roll domain and therefore not cross-linking. Similar results are observed with the wild type RTX sequence. In contrast, when calcium is added, concentrated peptide solutions exhibit rheological behavior indicative of a hydrogel, which has not been observed with the wild type sequences.

The resultant engineered beta roll peptide domains can cross-link in the presence of calcium. When combined with other cross-linking domains, this provides for allosterically controlled protein hydrogel formation. The hydrogels may be useful where it would be advantageous to deposit a gel as a viscous liquid, and subsequently cross-link the gel through the addition of calcium. Further utility may include addition of the beta roll appendages to globular proteins to obtain bi-functional constructs that form hydrogels in a calcium-dependent manner. Potential applications include, but are not limited to, bioelectrocatalytic, biomedical, and other biotechnological applications such as biosensors, etc.

Figure 2:
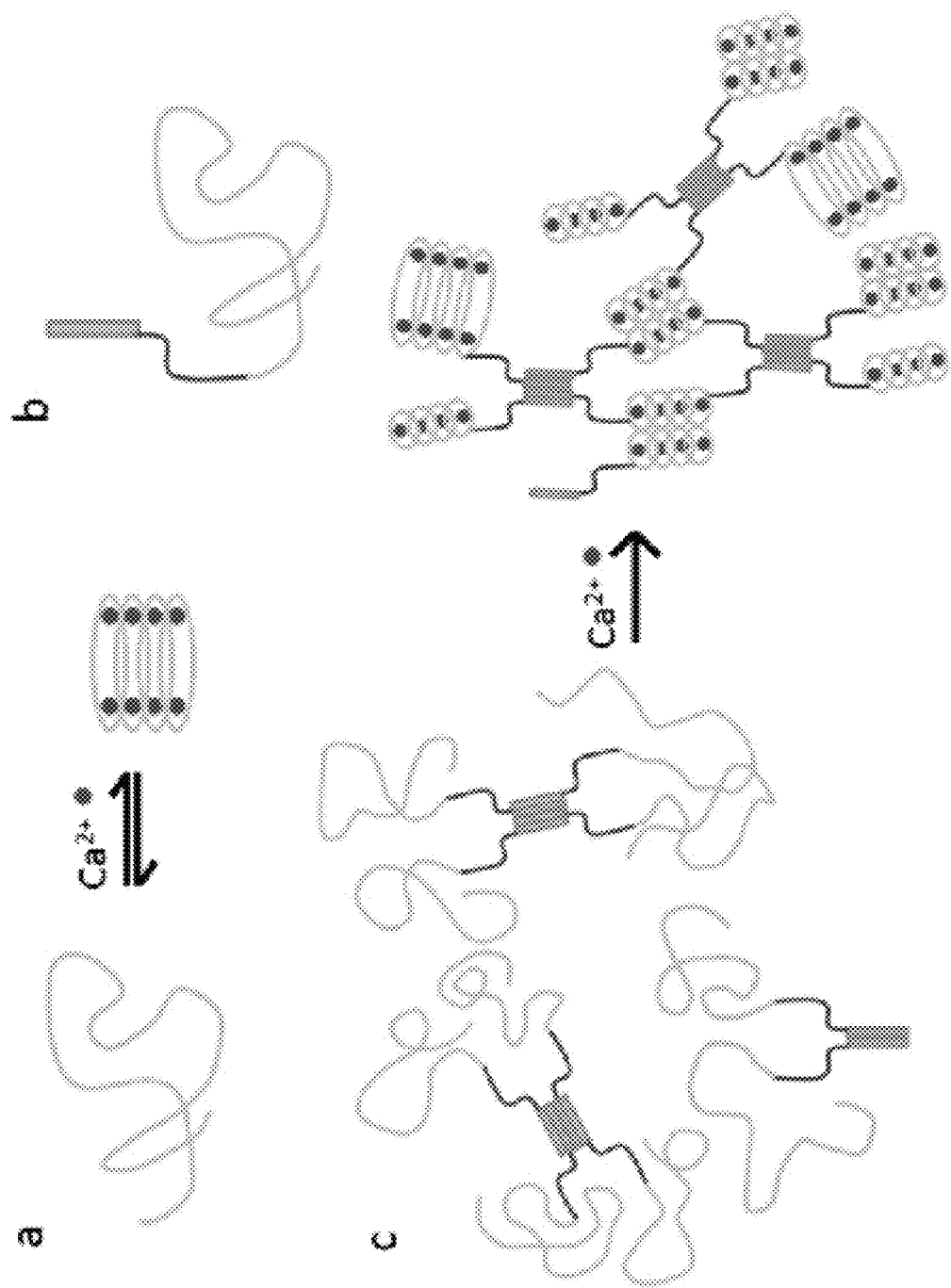
FIG. 2 shows hydrogel formation: (a) Calcium-induced conformational change of beta roll. In the absence of calcium, the beta roll remains disordered. Upon the addition of calcium, the beta roll undergoes a reversible structural change forming the corkscrew-like beta roll structure. The beta roll is depicted face forward. Calcium ions are shown in red. (b) Hydrogel monomeric building block. The α-helical leucine zipper domain (H) is shown in yellow with the soluble linker domain (S) in blue. The mutant leucine beta roll with the C-terminal capping region is shown in green. (c) Hydrogel transition. Prior to the addition of calcium, the helical domains can form tetrameric bundles, but the beta roll domains remain unstructured. When calcium is added, the folded beta roll domains expose the leucine rich faces, enabling cross-linking and hydrogel network formation. Some folded beta rolls are depicted from a side view, showing how two leucine faces could cross-link.

In order to assemble a hydrogel network, an α-helical leucine zipper (H) with a soluble linker region (S) is fused to the N-terminus of the leucine beta roll. In the absence of calcium, the beta roll remains unstructured. The leucine zippers can form colied-coil bundles, but the lack of interaction between the disordered beta roll domains prohibits the formation of a hydrogel. Upon addition of calcium, the beta roll undergoes a conformational change exposing the leucine face which enables dimerization. The dimerized beta rolls along with the leucine zipper bundles provide the physical cross-links necessary to form a hydrogel (FIG. 2). Unlike most stimulus responsive hydrogels which rely on changes in temperature and pH, mediation of the gel formation is allosterically mediated using calcium. Allosteric regulation allows for precise tuning of gel formation and strength by simply adjusting the calcium concentration, making these gels suitable for applications in systems that do not permit fluctuations in temperature or pH.

Through circular dichroism (CD) spectroscopy, bis-ANS binding, and terbium binding it is shown that the leucine mutations have minimal effect on the beta roll's response to calcium. After appending the H and S domains to the wild type (WT) and leucine beta roll, rheological analysis confirms that hydrogel formation is a direct result of the leucine mutations as the WT beta roll does not self-assemble in calcium rich environments.

Polypeptide Production

The beta roll peptide domains described herein can be produced in prokaryotic or eukaryotic host cells by expression of nucleic acids encoding a polypeptide of this invention. The production of these domains can also be done as part of a larger polypeptide.

The beta roll peptide domains described herein can also be synthesized in vitro, e.g., by the solid phase polypeptide synthetic method or by recombinant DNA approaches described herein. The solid phase polypeptide synthetic method is an established and widely used method. These beta roll peptide domains described herein can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

The beta roll peptide domains described herein can also be produced using any in-vitro expression system known in the art or can be synthesized by chemical methods. Methods for expression of heterologous proteins in recombinant hosts, chemical synthesis of polypeptides, and in vitro translation are well known in the art and are described further in Sambrook J et al.; Berger and Kimmel, Methods in Enzymology, Volume 152, Guide to Molecular Cloning Techniques (1987), Academic Press, Inc., San Diego, Calif.; Gutte B and Merrifield R B, J. Am. Chem. Soc. 91:501-02 (1969); Chaiken I M, CRC Crit. Rev. Biochem. 11:255-301 (1981); Kaiser E T et al., Science 243:187-92 (1989); Merrifield B, Science 232: 341-47 (1986); Kent S B H, Ann. Rev. Biochem. 57:957-89 (1988); Offord, R. E. (1980) Semisynthetic Proteins, Wiley Publishing; each herein incorporated by reference in its entirety. Examplary peptide synthesis methods known in the art include, but are not limited to those described in Stewart et al., Solid Phase Peptide Synthesis, Pierce Biotechnology, Inc., Rockford, Ill., 1984; Bodanszky, Principles of Peptide Synthesis, Springer-Verlag, New York, 1984; and Pennington et al., Peptide Synthesis Protocols, Humana Press, Totowa, N.J., 1994; each herein incorporated by reference in its entirety. Additionally, many companies offer custom peptide synthesis services.

The beta roll peptide domains described herein can also be produced by direct chemical synthesis. For example, the beta roll peptide domains described herein can be produced as modified polypeptides, with nonpeptide moieties attached by covalent linkage to the N-terminus and/or C-terminus. In certain embodiments, either the carboxy-terminus or the amino-terminus, or both, are chemically modified. Common modifications of the terminal amino and carboxyl groups, include, but are not limited to acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments. Certain amino-terminal and/or carboxy-terminal modifications and/or polypeptide extensions to the core sequence can provide advantageous physical, chemical, biochemical, and pharmacological properties, such as: enhanced stability, increased potency and/or efficacy, resistance to serum proteases, desirable pharmacokinetic properties, and others.

The beta roll peptide domains can also be prepared using recombinant DNA and molecular cloning techniques. Genes encoding the beta roll peptide domains may be produced in heterologous host cells, particularly in the cells of microbial hosts.

In the further step of the method the DNA coding for beta roll peptide domains described herein can be introduced into an appropriate host cells by transformation or by transfection and expressing the beta roll peptide domains. Techniques for transfecting host cells and purifying proteins and polypeptides are known in the art.

The beta roll peptide domains described herein can be produced by methods described herein and can be secreted and isolated from a mixture of cells and medium containing the protein or polypeptide. Alternatively, the protein or polypeptide can be retained cytoplasmically and the cells harvested, lysed, and the protein isolated. A cell culture can include host cells, media, and other byproducts. Suitable media for cell culture are well known in the art. Protein and polypeptides can be isolated from cell culture media, host cells, or both using techniques known in the art for purifying proteins and polypeptides.

Nucleic Acids

The beta roll peptide domains described herein can also be produced by recombinant DNA techniques. Alternative to recombinant expression, a beta roll peptide domains described herein can be synthesized chemically using standard polypeptide synthesis techniques.

The nucleotide sequence of a DNA or RNA molecule coding for a nucleic acid of this invention (or a portion thereof) can be used to derive a beta roll peptide domains described herein using the genetic code to translate the DNA or RNA molecule into an amino acid sequence. Thus, description and/or disclosure herein of a nucleic acid sequence of this invention also includes the description and/or disclosure of the amino acid sequence encoded by the nucleic acid sequence. Similarly, description and/or disclosure of a amino acid sequence of this invention herein also includes the description and/or disclosure of all possible nucleic acid sequences that can encode the amino acid sequence.

A variety of expression systems can be used to produce the beta roll peptide domains described herein. Such expression systems include vector based expression systems. Exemplary vector base expression systems suitable for use with the methods described herein include, but are not limited to, chromosomal, episomal and virus-derived vectors, e.g., vectors derived from bacterial plasmids, from bacteriophage, from transposons, from insertion elements, from yeast episomes, from viruses such as baculoviruses, retroviruses and vectors derived from combinations thereof such as those derived from plasmid and bacteriophage genetic elements, such as cosmids and phagemids.

The expression system vectors may contain regulatory regions that regulate as well as engender expression. In general, any system or vector suitable to maintain, propagate or express polynucleotide or polypeptide in a host cell may be used for expression in this regard. Expression systems and expression vectors can contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the beta roll peptide domains of the present invention. These chimeric genes could then be introduced into appropriate microorganisms via transformation to provide high level expression of the domains.

A number of recombinant expression vectors can be used for expression of the beta roll peptide domains described herein. For example, beta roll peptide domains described herein can be expressed in bacterial cells such as E. coli, insect cells (e.g., using baculovirus expression vectors), yeast cells, amphibian cells, or mammalian cells. Suitable host cells are well known to one skilled in the art. Alternatively, the recombinant expression vector can be transcribed and translated in vitro, using, for example T7 promoter regulatory sequences and T7 polymerase.

Examples of E. coli expression vectors include pTrc (Amann E et al., Gene 69:301-15 (1988); herein incorporated by reference in its entirety) and pET 11d (Studier et al., Gene Expression Technology Methods in Enzymology 185, Academic Press, San Diego, Calif. (1990) pp. 60-89; herein incorporated by reference in its entirety). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman S, Gene Expression Technology: Methods in Enzymology 185, Academic Press, San Diego, Calif. (1990) pp. 119-28; herein incorporated by reference in its entirety). Another strategy is to alter the nucleic acid sequence of the nucleic acid to be inserted into an expression vector so that the individual codons for each amino acid are those preferentially utilized in E. coli (Wada K et al., Nucleic Acids Res. 20(Suppl.):2111-18 (1992); herein incorporated by reference in its entirety). Such alteration of nucleic acid sequences can be carried out by standard DNA synthesis techniques.

In another approach, a nucleic acid can be expressed in mammalian cells using a mammalian expression vector. Examples of mammalian expression vectors include pCDM8 (Seed B, Nature 329:840-41 (1987); herein incorporated by reference in its entirety) and pMT2PC (Kaufman R J et al., EMBO J. 6:187-95 (1987); herein incorporated by reference in its entirety). When used in mammalian cells, the expression vector's control functions can be provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual, 2nd ed., Cold Spring Harbor Laboratory, Cold Spring Harbor Laboratory Press, Cold Spring Harbor, N.Y., 1989; herein incorporated by reference in its entirety.

A number of these methodologies can also be applied in vivo, systemically or locally, in a complex biological system such as a human. For example, increased copy number of nucleic acids encoding the beta roll peptide domains described herein in expressible form (by DNA transfection), can be employed.

A rationally designed leucine rich beta roll domain using the adenylate cyclase RTX from B. pertussis as a template was constructed, expressed and purified. Experiments were conducted to compare the mutant construct to the WT to ensure the mutations did not disrupt the peptide's response to calcium. CD spectra, bis-ANS binding, and terbium binding experiments all suggest a similar calcium induced conformational change and calcium binding affinity. In the absence of calcium, both leucine and WT beta roll CD spectra exhibit a large negative peak at 198 nm indicative of randomly coiled polypeptide. Upon addition of 50 mM calcium, both constructs show a similar increase of beta sheet secondary structure with a negative peak emerging at 218 nm (FIG. 4a, b). These results are consistent with what has been reported previously by Blenner, M. A. et al., J. Mol. Biol. 2010, 400, 244-256; herein incorporated by reference in its entirety. A calcium titration was performed by monitoring the change in CD signal at 218 nm (FIG. 4e). Bis-ANS binding spectra also suggest similar structural changes in response to calcium (FIG. 4c, d). As the beta roll binds calcium and folds into its secondary structure, hydrophobic patches suitable for bis-ANS binding are exposed, which leads to an increase in fluorescence in calcium rich environments.

Fluorescence resonance energy transfer (FRET) experiments were performed to supplement the CD and bis-ANS binding data. Terbium, a lanthanide atom, was titrated into beta roll samples. The subsequent fluorescence emission from tyrosine residues in close proximity to bound terbium ions was measured spectrophotometrically (FIG. 4f). It is important to note that while terbium is often used as a calcium analog, it does not directly indicate calcium binding. However, when analyzed in coordination with the CD and bis-ANS data, it does bolster the claim that both constructs undergo a similar calcium induced structural change. The terbium titrations are consistent with the bis-ANS binding results. Also, both WT and leucine beta rolls bind the calcium analog with a similar affinity. The constructs were further analyzed after appending the leucine zipper and soluble linker domains.

Figure 5:
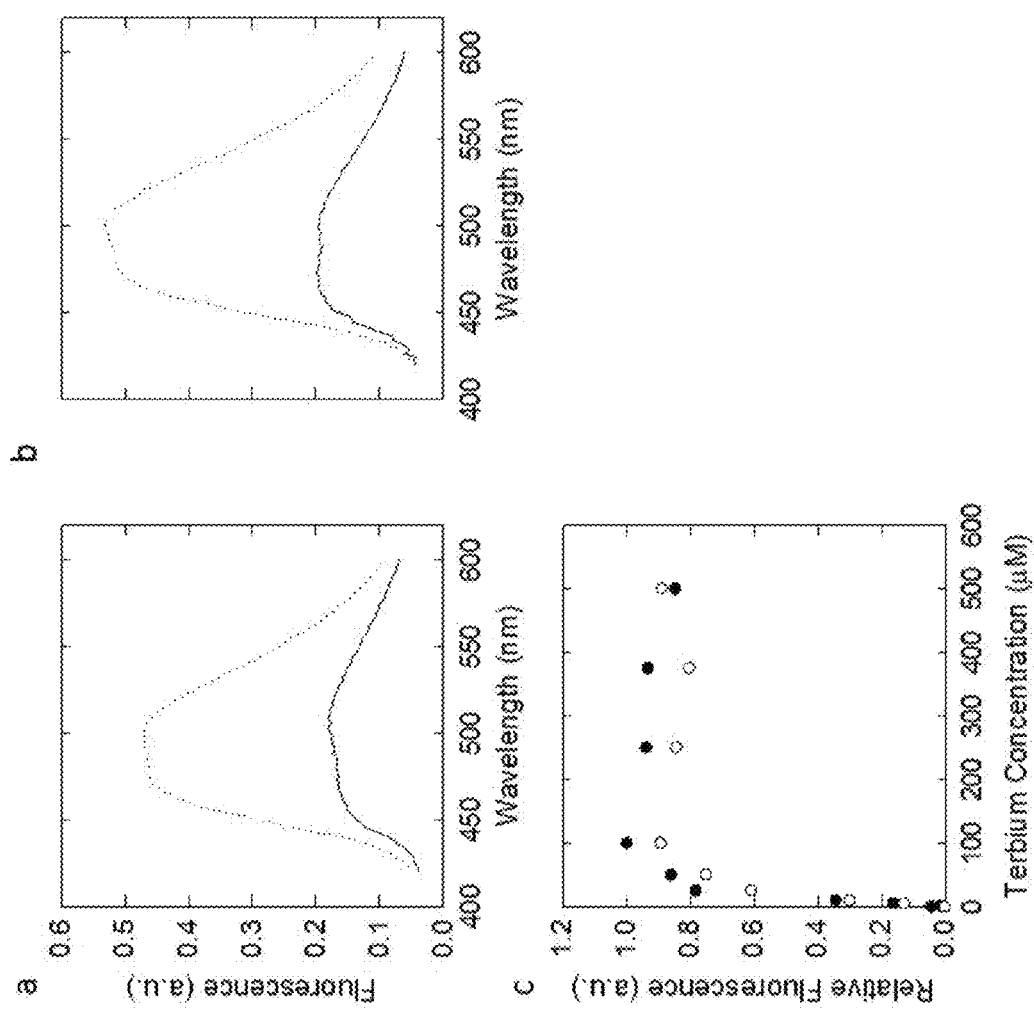
FIG. 5 shows HS-WT and HS-leucine beta roll calcium responsiveness and characterization. (a) HS-WT and (b) HS-leucine beta roll bis-ANS binding spectra in the presence (•••) and absence (—) of 50 mM calcium. This data is consistent with the terbium binding shown in (c) for the WT (○) and leucine (•) constructs.

WT and leucine constructs are analyzed by native PAGE to confirm the oligimerization state of the mutant beta roll in the presence of calcium (Dooley, K. et al. *Biomacromolecules* 2012, 13, 1758-64; herein incorporated by reference in its entirety). Both samples migrate similarly through the native gel in the absence of calcium. Upon the addition of 5 mM calcium to the running buffer, there is a clear difference in migration between the WT and leucine beta roll. The leucine beta roll appears to run larger, suggesting the formation of an oligomer, most likely caused by the cross-linking of the leucine-rich faces. Whereas these gels are not entirely quantitative, they do suggest an apparent difference in size, only in the presence of calcium. An α-helical leucine zipper domain (H) along with a randomly coiled polyelectrolyte domain (S) were added to the N-terminus of the leucine and WT beta rolls. Similar characterization experiments were performed in order to determine if these domains would have any effects on calcium response and structural change. The CD spectra did show changes in response to calcium, but the signal was dominated by the largely helical content of the H domain (Dooley, K. et al. *Biomacromolecules* 2012, 13, 1758-64; herein incorporated by reference in its entirety). Bis-ANS binding experiments were performed as described previously. The resulting spectra (FIG. 5a, b) again show no discernable difference between the HS-leucine and HS-WT proteins. The same baseline shift is observed for the HS-leucine beta roll, but the relative changes in peak intensity upon addition of calcium are the same. The terbium titration (FIG. 5c) is consistent.

HS-WT and HS-leucine beta roll samples were characterized using a multi-particle tracking microrheology technique. The Brownian motion of small particles infused into the sample were recorded using video microscopy and the average mean square displacement (MSD) of the particles were calculated as a function of time. In a purely viscous sample, there is a linear relationship between the MSD and the lag time ($\tau$) with a slope of 1 on a log-log plot. As the sample becomes more elastic, the slope of MSD vs. $\tau$ begins to deviate from 1, approaching 0 in a purely elastic medium. The MSD of the tracer particles sheds light on the mechanical properties of the fluid they are embedded in. Once the MSD is obtained, the frequency dependent viscous and elastic moduli of a sample can be calculated using the modified Stokes-Einstein equation. Both constructs demonstrated concentration dependent gelation. A small pilot study showed that at weight percentages below 5%, the samples remained viscous with and without calcium. Conversely, at weight percentages above 10%, the samples were completely elastic. At weight percentages of 6%, calcium dependent gelation was observed and further explored.

6 wt % samples of HS-WT and HS-leucine beta roll were prepared. After the samples were supplemented with the tracer particles, video microscopy was used to record the particles' motion. The trajectories and mechanical properties were calculated using Interactive Data Language (IDL) software. The viscous (G") and elastic (G') moduli of HS-WT and HS-leucine (in buffer) as a function of frequency are shown in FIGS. 6a and 6b, respectively. Both constructs appear to be viscous liquids in buffer (FIG. 6a,b) and in the presence of 50 mM magnesium (FIG. 6c,d). However, whereas the WT construct remains viscous in 50 mM calcium (FIG. 6e), the leucine construct forms a hydrogel (FIG. 6f). To supplement this data, a calcium titration was performed with 6 wt % HS-leucine beta roll samples. The calcium concentration was varied from 0-10 mM and the resultant rheological plots are given in FIG. 7. A large shift in the elastic and viscous modulus is seen even at 500 μM calcium with a crossover frequency of about 3 s$^{-1}$. As the calcium concentration is increased, the crossover frequency continues to shrink. At 10 mM calcium, the sample is essentially elastic.

Several biophysical techniques were used in this work to probe the calcium binding, structural confirmation, and mechanical properties of the WT and leucine beta roll constructs. We have shown that the leucine mutations made to the WT beta roll resulted in no change in calcium responsiveness or binding affinity; similar conformational changes are observed in the mutant beta roll as shown by CD and bis-ANS binding. This was as expected because the residues selected for mutation do not participate in calcium binding. Assuming the beta roll adopts a structure similar to those derived crystallographically in other RTX containing proteins, the amino acid side chains that are mutated projectr radially outward, away from the hydrophobic core minimizing any potential steric effects. Furthermore, native PAGE data indicates a calcium-dependent difference in migration between the mutant and WT proteins, likely caused by leucine beta roll cross-linking. This premise was elucidated through the rheological experiments after cloning both constructs into the pQE9 vector.

Appending the H and S domains to the N-termini of the WT and leucine beta roll also had minimal effects on response to calcium as shown by the bis-ANS and terbium binding data. This was also expected. It has been previously shown that native N-terminal capping group does not play an important role in protein folding. Although the CD spectra of the constructs containing the H and S domains are dominated by the highly helical H domain, there appear to be conformational changes following the addition of calcium. Further, SEC data has shown a calcium dependent difference in speciation between the mutant and WT proteins, possibly caused by leucine beta roll dimerization. This premise was further elucidated through rheological studies.

The microrheology data presented substantial differences in viscoelastic properties between the HS-WT and HS-leucine beta rolls in the presence of calcium. At 6 wt %, both constructs exhibited viscous character in buffer and in buffer supplemented with 50 mM magnesium. The magnesium control shows that the ionic effects did not influence the changes in mechanical properties of both samples. When calcium is added to the HS-WT protein, it remains viscous. Here, without being bound by theory, the WT beta roll is fully folded, as indicated by the CD data. However, this calcium induced structural response does not promote the formation of a hydrogel network because the WT beta roll domains do not interact. There is a minimal driving force for interaction between folded WT beta roll domains. Upon addition of calcium to the HS-leucine beta roll, there is a significant change in rheological properties. The sample appears to be elastic, showing frequency-independentviscous and elastic moduli. Again, at 50 mM calcium the leucine beta roll is expected to be completely folded, and the engineered hydrophobic leucine face is exposed to the solvent. This creates a hydrophobic driving force for the dimerization of two leucine beta rolls and promotes cross-linking of the beta roll domains. The calcium-dependent physical cross-linking between beta rolls coupled with the coiled coil bundles formed by the leucine zipper domains provides enough interaction to alter the mechanical properties of the sample and create a hydrogel network. It may also be possible for the leucine zipper domains to interact with the leucine beta roll domains, and this would introduce a different mode of cross-linking within the hydrogels.

The transition from viscous liquid to hydrogel shown in FIG. 7 is consistent with the leucine beta roll CD titration data in FIG. 4e. It was shown that the leucine beta roll transitions from disordered to structured peptide between 0.5-3.0 mM calcium. At concentrations higher than 3 mM the beta roll has become completely folded. A strong parallel can be drawn with the rheology data in FIG. 7. The sample is transitioning from a viscous liquid to a hydrogel between 0.5-5 mM calcium. By 10 mM, the hydrogel is completely formed because the beta roll domains are completely folded, maximizing the physical cross-linking. The slightly higher concentration required to form the hydrogel can be attributed to the fact that the CD data is collected in dilute solution, making the beta roll easily accessible to the calcium ions.

Herein is presented a rationally designed protein that can be used to create allosterically controlled hydrogel networks. Leucine mutations were inserted into the WT beta roll scaffold to create a hydrophobic surface suitable for dimerization, exposed only after calcium binding. An α-helical leucine zipper domain with a randomly coiled linker were attached to the N-terminus of the beta roll to provide one avenue of physical cross-linking. The leucine zippers alone cannot create the complex network required for gelation. Hydrogels are formed only in calcium rich environments where the folded leucine beta roll domains provide the necessary cross-linking interface. The WT beta roll remained a viscous liquid regardless of the calcium concentration.

Most stimulus responsive hydrogels presented in the literature respond to changes in temperature or pH. These hydrogels use cross-link forming scaffolds; then, a trigger is found to destabilize the binding interaction. For example, the leucine zipper-based hydrogels are destabilized by changes in pH because this interferes with the alpha-helix formation, and the elastin-like peptide based hydrogels take advantage of the unique inverse temperature transition of these peptides to destabilize the hydrogel. This may prove to be limiting in terms of some practical applications. Herein allosteric regulation of a stimulus responsive hydrogel has been demonstrated using calcium. We have chosen a scaffold that undergoes a specific and unique conformational transition from an intrinsically disordered structure to the folded beta roll domain in response to calcium. The beta roll domain is not normally involved in biomolecular recognition or self-assembly, so this feature was engineered into the scaffold to control self-assembly by calcium addition. Eliminating the reliance on temperature and pH swings to modulate self-assembly allows for the use of these hydrogels in more biologically relevant environments, where chanes in temperature or pH are not tolerated. This peptide may function at a wider range of temperature and pH while maintaining its response to calcium. Since the beta roll is a modular repeat protein, the number of repeats and composition of the repeating unit can be modified, which may alter the mechanical properties of the hydrogels. Previous work has also shown the beta roll exhibits a reversible response to calcium, meaning the peptide will return to a disordered state upon removal of calcium ions. Reversibility of the hydrogel formation may be advantageous. Also, the beta roll has a second face amenable to mutation, which could be used to create leucine-rich surfaces on both sides of the folded beta roll. Enzymes, growth factors and other domains could be grafted between 2 "double-faced" leucine constructs creating functional hydrogels while eliminating the need for leucine zippers.

The leucine beta rolls, herein presented, have a relatively low elastic moduli but could be optimized to create stronger hydrogels for different applications. Because the beta roll is a modular repeat protein, the number of repeats and composition of the repeating unit can be altered to extend the size and makeup of the hydrophobic domain. Alternative cross-linking strategies could be incorporated such as the inclusion of specific ionic interactions as has been explored for leucine zipper domains.

Another aspect of the invention relates to methods of making beta rolls comprising a scaffold from the RTX domain of adenylate cyclase, wherein leucine mutations are introduced on the beta roll domain.

Another aspect of the invention relates to methods of making a protein hydrogel network comprising the beta rolls, wherein the beta rolls comprise a scaffold from the RTX domain of adenylate cyclase, wherein leucine mutations are introduced on the beta roll domain. In some embodiments, the beta roll is fused to a leucine zipper with a soluble linker region.

It will be recognized that one or more features of any embodiments disclosed herein may be combined and/or rearranged within the scope of the invention to produce further embodiments that are also within the scope of the invention.

Those skilled in the art will recognize, or be able to ascertain using no more than routine experimentation, many equivalents to the specific embodiments of the invention described herein. Such equivalents are also intended to be within the scope of the present invention.

The following examples illustrate the present invention, and are set forth to aid in the understanding of the invention, and should not be construed to limit in any way the scope of the invention as defined in the claims which follow thereafter.

EXAMPLES

Maltose binding protein (MBP) expression kit and all enzymes were purchased from New England Biolabs (Ipswich, Mass.). Isopropyl β-D-1-thiogalactopyranoside (IPTG) was obtained from Promega (Madison, Wis.). Halt protease inhibitor cocktail was purchased from Fisher Scientific (Waltham, Mass.). AMICON centrifugal filters were purchased from Millipore (Billerica, Mass.). Native PAGE gels, running buffer, protein ladder, and SIMPLYBLUE SafeStain were obtained from Life Technologies (Grand Island, N.Y.). All chemicals and other reagents were purchased from Sigma-Aldrich (St. Louis, Mo.) unless otherwise indicated.

Example 1

Cloning into pMAL and pQE9 Vectors

Both WT and leucine beta roll proteins were expressed using a modified pMAL vector. The intein domain from ELP-intein-OPH, a gift from Dr. David Wood (Ohio State University, OH), was cloned out using PCR primers with SacI and KpnI restriction sites for subsequent ligation with T4 DNA ligase into pMAL. The WT beta roll and the C-terminal capping region were cloned out of the pDLE9-CysA, a gift from Dr. Daniel Ladant (Institut Pasteur, Paris, France) using PCR primers with KpnI and HinduIII restriction sites for ligation into the pMAL-intein vector.

The leucine beta roll was constructed by inserting the appropriate leucine mutations into two overlapping oligonucleotides encoding for the entire beta roll. The oligonucleotides were annealed and extended to produce the full-length double-stranded leucine beta roll. The C-terminal capping group was added by overlap extension PCR. KpnI and HindIII sites were added to the capped leucine beta roll before ligation into intein-pMAL.

Figure 3:
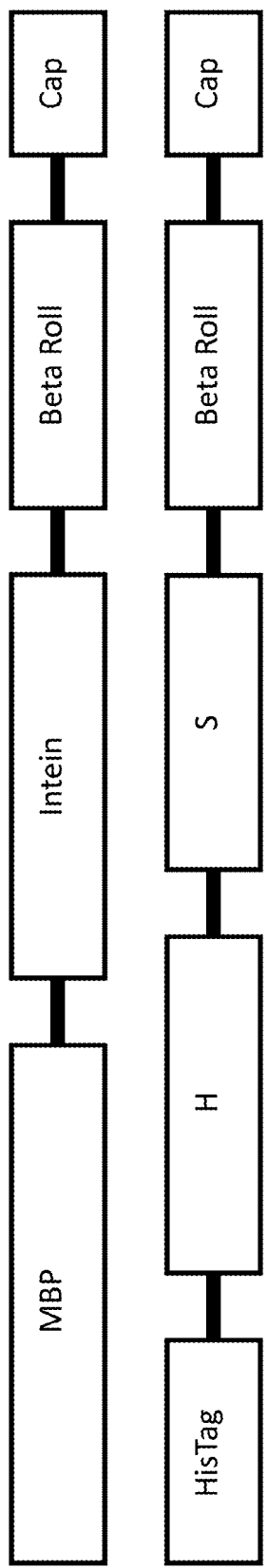
FIG. 3 shows a schematic of beta roll expression and purification constructs. WT and leucine beta rolls were expressed as fusions to maltose binding protein and purified by intein cleavage. HS-WT and HS-leucine beta rolls were expressed using the pQE9 vector and purified using polyhistidine tags. H represents an α-helical leucine zipper domain and S represents a randomly coiled linker domain.

Both HS-WT and HS-leucine beta rolls were expressed using a modified pQE9AC10Acys vector, a gift from David Tirrel (California Institute of Technology, CA). In this work AC10Acys is termed H—S—H. Both beta roll genes were amplified by PCR using primers with SphI and SpeI restriction sites for subsequent cloning into pQE9, which had been previously modified to remove the C-terminal helical domain. pMAL vectors were transformed into OmniMAX (Invitrogen) and pQE9 vectors were transformed into SG13009 (QIAGEN) strains of E. coli for expression. A schematic of the completed constructs is provided in FIG. 3.

Expression and Purification of WT and Leucine Beta Rolls

The WT beta roll and leucine beta roll constructs were expressed identically in sterile LB media with 2 g/L D-glucose. 1 L cultures, supplemented with 100 µg/mL ampicillin prior to inoculation, were inoculated with 2 mL from an overnight culture of the appropriate pMAL-intein vector. The 1 L cultures were incubated at 37° C. with shaking until $OD_{600}=0.6$. Protein expression was induced by the addition of isopropyl β-D-1-thiogalactopyranoside (IPTG, Promega) to a final concentration of 0.3 mM. Expression was carried out for 2 h at 37° C. with shaking. The cells were pelleted at 3,000 g for 15 minutes and the supernatant was discarded. The cell pellets were resuspended in 25 mL MBP column buffer (20 mM Tris-HCl, 200 mM NaCl, 1 mM EDTA, pH7.4) and supplemented with a protease inhibitor cocktail (Halt™). Cell lysis was performed via sonication with a microtip sonicator for 6 minutes on ice (Misomix Sonicator 3000). The lysate was clarified by centrifugation at 15,000 g for 30 minutes after which the pellet was discarded. Soluble fractions were pooled, diluted 5-fold with MBP column buffer and loaded onto amylose resin columns, as described by the manufacturer (New England Biolabs). The columns were washed, capped and filled with 8 mL of intein cleaving buffer (137 mM NaCl, 2.7 mM KCl, 8.1 mM $Na_2HPO_4 \cdot H_2O$, 1.76 mM $KH_2PO_4$, 40 mM bis-Tris, 2 mM EDTA, pH6.2) and incubated at 37° C. for 12-16 h. The cleaved beta roll was eluted with 50 mL of MBP column buffer, concentrated in 10 kDa MWCO AMICON centrifugal filters (Millipore) and buffer exchanged with 20 mM bis-Tris, 25 mM NaCl, pH6.0. The samples were run over a 16/10 Q FF ion-exchange column (GE Healthcare) using an ÅKTA$_{FPLC}$ (GE Healthcare). Separation between MBP fusions and cleaved beta roll was achieved using an NaCl gradient from 25 mM to 500 mM over 20 column volumes. Beta roll fractions were collected and desalted prior to SDS-PAGE. The sample concentrations were determined by adsorption at 280 nm using calculated extinction coefficients (WT, $\epsilon_{280}=17\,780$ $M^{-1}$ $cm^{-1}$; leucine, $\epsilon_{280}=16\,500$ $M^{-1}$ $cm^{-1}$. Typical yields ranged from 3 to 7 mg of pure protein per liter of culture.

Expression & Purification of HS Constructs

Both HS-WT and HS-leucine beta roll constructs were expressed identically and purified using immobilized metal affinity chromatography and a polyhistidine tag. 1 L sterile cultures of Terrific Broth (TB) were supplemented with 50 µg/mL kanamycin and 200 µg/mL ampicillin prior to inoculation with 2 mL from an overnight culture of the appropriate vector. Protein expression was induced by the addition of IPTG to a final concentration of 0.5 mM after $OD_{600}=0.6$ was reached. Expression was carried out for 5 h at 37° C. with shaking. The cells were pelleted and resuspended in 25 mL of HisA buffer (20 mM Tris-HCl, 150 mM NaCl, 40 mM imidazole, pH7.5) supplemented with a protease inhibitor cocktail (Halt™). Cell harvesting, lysis and clarification were performed using the same method mentioned previously. Samples were loaded on to a 5 mL nickel charged HISTRAP FF column (GE Healthcare) equilibrated with HisA. The loaded sample was washed with 10 column volumes of HisA and the his-tagged protein was eluted with HisB buffer (20 mM Tris-HCl, 150 mM NaCl, 500 mM imidazole, pH7.5) using a linear gradient to 100% HisB over 20 column volumes. Fractions containing the desired protein were collected and confirmed by SDS-PAGE. Samples were desalted and concentrated by ultrafiltration using 30 kDa MWCO AMICON centrifugal filters (Millipore). Increased purity can be achieved by size exclusion chromatography. Typical yields ranged from 20 to 30 mg of pure protein per liter of culture.

CD Spectroscopy

These techniques were performed as described previously. In brief, 100 µM samples were loaded into a 0.01 cm path length quartz cuvette and analyzed on a J-815 CD spectrometer (Jasco) equipped with a Peltier junction temperature controller. All measurements are performed in triplicate in 50 mM Tris pH7.5 at 25° C. Titration data was fit using SIGMAPLOT (Systat Software) nonlinear regression software.

Bis-ANS Binding Fluorescence Spectroscopy

Protein samples (250 nM) were loaded in a 1 cm path length cuvette and equilibrated with 0 or 50 mM calcium prior to the addition of 1 µg/mL bis-ANS. Changes in fluorescence emission were measured from 420 to 600 nm using a FMO-427S monochromator (Jasco). Excitation was at 390 nm. All measurements are performed in triplicate in 50 mM Tris pH7.5 at 25° C.

Terbium Binding Fluorescence Resonance Energy Transfer (FRET)

1 µM protein samples were titrated with terbium chloride. Following excitation of the sample at 282 nm, changes in fluorescence emission from bound terbium ions were monitored at 545 nm. All experiments were performed in 96-well plates (Costar) in 20 mM PIPES pH 6.8, 120 mM NaCl, 10 mM KCl. Terbium was incubated with the protein samples for 30 min at 25° C. prior to reading. All data were fit using SIGMAPLOT nonlinear regression software.

Native Polyacrylamide Gel Electrophoresis (PAGE)

Samples (2 μg) of leucine and WT beta roll are run on 4-16% Bis-Tris 1.0 mm gels. The voltage is held constant at 150 V, and the run time is set to 105 min. For runs completed with calcium, 5 mM CaCl$_2$ is added to the running buffer. The gels are stained with SIMPLYBLUE SafeStain according to the manufacturer's protocol.

Hydrogel Preparation

Hydrogel constructs were allowed to self-assemble by reconstituting lyophilized protein with small volumes of water. HS-WT and HS-leucine beta roll concentrations were determined by UV absorbance at 280 nm using the extinction coefficients $\epsilon_{280}$=24,750 M$^{-1}$ cm$^{-1}$ and $\epsilon_{280}$=23,470 M$^{-1}$ cm$^{-1}$ respectively (Spectromax M2, Molecular Devices). Protein (1.5 mg) was diluted in 250 μl of 5 mM Tris pH 7.5 with the appropriate salt concentration, frozen overnight at −80° C. and lyophilized the following day. The lyophilized protein was rehydrated with 25 μL of Millipore water yielding 6 wt % samples. Mechanical mixing, vortexing, and centrifugation were used to unsure all of the protein was rehydrated. The samples were centrifuged for 5 minutes at 13,000 g to remove any air bubbles and allowed to set.

Microrheology

Microrheology is a technique that analyzes the mechanical properties of a viscoelastic fluid by monitoring the motion of micrometer sized spherical particles embedded in the sample. In active microrheology, the particles are stimulated by an applied magnetic field or by optical tweezers, which use a highly focused laser. In this study, passive microrheology was used which relies on Brownian motion of the particles caused by small, intrinsic thermal fluctuations. The particles' mean square displacements (MSD) can be calculated experimentally and are related to the mechanical properties of the fluid through a generalized Stokes-Einstein equation:

$$\langle \Delta \tilde{r}^2(s) \rangle = \frac{dk_B T}{3\pi a s \tilde{G}(s)}$$

Where $\langle \Delta \tilde{r}^2(s) \rangle$ is the time averaged Laplace transform of the particles' MSD, d is the dimensionality of the track (2 for this work), $k_B$ is the Boltzmann constant, T is the temperature, α is the radius of the tracer particle, s is the Laplace frequency, and $\tilde{G}(s)$ is the frequency dependent Laplace representation of the complex modulus. This is composed of both the elastic (G') and viscous (G") moduli.

When reconstituting the lyophilized protein, 1 μm fluorescently labeled polystyrene (Fisher) tracer particles were added. The samples were mixed thoroughly, allowed to set, loaded onto a glass microscope slide between two strips of Parafilm® and sealed with a glass coverslip. Particle motion was observed using a green-fluorescent optical microscope (Nikon Eclipse 50i) with a 40× objective. 300 frames of video were recorded per run at an exposure time of 33 ms with a NIKON HRD076 camera. Three separate videos were taken per sample to ensure a good statistical average. Readings were made in the middle of each sample so that any edge effects could be neglected. Image stacks were created using ImageJ and analyzed using IDL software. The particle trajectories and rheological properties of each sample were calculated using algorithms created by Crocker, J. C. et al, *A. Phys. Rev. Lett.* 2000, 85, 888; herein incorporated by reference in its entirety.

As will be apparent to one of ordinary skill in the art from a reading of this disclosure, further embodiments of the present invention can be presented in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention. The scope of the invention is as set forth in the appended claims and equivalents thereof, rather than being limited to the examples contained in the foregoing description.

What is claimed is:

1. A beta roll comprising a scaffold from the RTX domain of adenylate cyclase from *Bordetella pertussis*, wherein leucine mutations are introduced on the beta roll domain, wherein the beta roll domain comprises the amino acid sequence $X_1X_2X_3X_4X_5X_6X_7X_8X_9$ (SEQ ID NO: 10), wherein (a) $X_1$ is an amino acid selected from the group consisting of glycine, valine and serine;

(b) $X_2$ is an amino acid selected from the group consisting of glycine, serine, aspartic acid and leucine;

(c) $X_3$ is an amino acid selected from the group consisting of alanine, glutamic acid, glutamine, tyrosine and glycine;

(d) $X_4$ is an amino acid selected from the group consisting of glycine and arginine;

(e) $X_5$ is an amino acid selected from the group consisting of aspartic acid, alanine, asparagine, serine, and histidine;

(f) $X_6$ is an amino acid selected from the group consisting of aspartic acid and asparagine;

(g) $X_7$ is an amino acid selected from the group consisting of valine, leucine, and threonine;

(h) $X_8$ is an amino acid selected from the group consisting of leucine, isoleucine, and tyrosine;

(i) $X_9$ is an amino acid selected from the group consisting of isoleucine, leucine, serine, and arginine; and (j) $X_{10}$ is appended adjacent to $X_9$, and wherein $X_{10}$ is the amino acid glutamic acid.

2. The beta roll of claim 1, wherein $X_1$ is the amino acid glycine.

3. The beta roll of claim 1, wherein $X_4$ is the amino acid glycine.

4. The beta roll of claim 1, wherein $X_6$ is the amino acid aspartic acid.

5. The beta roll of claim 1, wherein $X_8$ is the amino acid leucine.

6. The beta roll of claim 2, wherein $X_4$ is the amino acid glycine.

7. The beta roll of claim 2, wherein $X_6$ is the amino acid aspartic acid.

8. The beta roll of claim 2, wherein $X_8$ is the amino acid leucine.

9. The beta roll of claim 3, wherein $X_6$ is the amino acid aspartic acid.

10. The beta roll of claim 1, wherein
    (a) $X_7$ is the amino acid leucine;
    (b) $X_8$ is the amino acid leucine; and
    (c) $X_9$ is the amino acid leucine.

11. A beta roll comprising a scaffold from the RTX domain of adenylate cyclase from *Bordetella pertussis*, wherein leucine mutations are introduced on the beta roll domain, wherein the beta roll domain comprises the amino acid sequence GDAGANLLL (SEQ ID NO:2), GGAGDDLLL (SEQ ID NO:4), GDAGNDLLL (SEQ ID NO:6), or VGYGHDLILE (SEQ ID NO:8).

\* \* \* \* \*